(12) United States Patent
Tan et al.

(10) Patent No.: US 11,311,687 B2
(45) Date of Patent: Apr. 26, 2022

(54) THREE-DIMENSIONAL STRUCTURE HEATING UNIT AND LIQUID GUIDING UNIT FOR ATOMIZER OF AN E-CIGARETTE

(71) Applicant: Shenzhen Innokin Technology Co., Ltd., Shenzhen (CN)

(72) Inventors: Huimin Tan, Shenzhen (CN); Lei Le, Shenzhen (CN); Yong Fang, Shenzhen (CN); Zhengzhan Peng, Shenzhen (CN)

(73) Assignee: SHENZHEN INNOKIN TECHNOLOGY CO., LTD., Shenzhen (CN)

( * ) Notice: Subject to any disclaimer, the term of this patent is extended or adjusted under 35 U.S.C. 154(b) by 338 days.

(21) Appl. No.: 16/547,470

(22) Filed: Aug. 21, 2019

(65) Prior Publication Data
US 2020/0060344 A1 Feb. 27, 2020

(30) Foreign Application Priority Data

Aug. 22, 2018 (CN) .......................... 201810961311.2
Nov. 27, 2018 (CN) .......................... 201821963045.9
Jan. 18, 2019 (CN) .......................... 201910048577.2
Jun. 20, 2019 (CN) .......................... 201910535711.1

(51) Int. Cl.
*A24F 13/00* (2006.01)
*A24F 17/00* (2006.01)
*A24F 25/00* (2006.01)
*A61M 11/04* (2006.01)

(52) U.S. Cl.
CPC ................................ *A61M 11/042* (2014.02)

(58) Field of Classification Search
CPC ........ A24F 40/10; A24F 40/46; A24F 40/465; A24F 40/70; A61M 11/042
See application file for complete search history.

(56) References Cited

U.S. PATENT DOCUMENTS

| 6,565,698 | B1* | 5/2003 | Adams ................. B07B 1/4627 |
| | | | 156/290 |
| 2010/0288270 | A1* | 11/2010 | Wada ..................... B41J 2/1433 |
| | | | 128/200.14 |
| 2017/0108210 | A1* | 4/2017 | Meinhart .................. F22B 1/30 |
| 2018/0263285 | A1* | 9/2018 | Kleizo .................... A24F 40/40 |

(Continued)

*Primary Examiner* — Abdullah A Riyami
*Assistant Examiner* — Thang H Nguyen
(74) *Attorney, Agent, or Firm* — Millburn IP PLLC

(57) ABSTRACT

The present invention provides a 3D atomizing heating component comprising a plate body having upper and lower surfaces, the plate body providing a plurality of 3D heating units for guiding, heating and atomizing the e-liquid. The 3D heating units have a through hole in the plate body and guide channels distributed regularly at the periphery of the through hole, which runs through the upper and lower surfaces of the plate body. The guide channels are recessed from the surface of the plate body and communicate with the through hole. The guide channels of the adjacent 3D heating units are connected with each other on the surface of the plate body, and the plurality of 3D heating units form a regular pattern on the surface of the plate body. The components provided improve the taste and user experience. Manufacturing is easy, facilitating the mass and mechanical production.

13 Claims, 15 Drawing Sheets

(56) References Cited

U.S. PATENT DOCUMENTS

| | | | |
|---|---|---|---|
| 2018/0280239 A1* | 10/2018 | Miyazaki | A61J 1/201 |
| 2019/0186840 A1* | 6/2019 | Chiang | H05K 7/20336 |
| 2019/0350260 A1* | 11/2019 | Di Marco | A61M 11/042 |
| 2020/0232708 A1* | 7/2020 | Kimura | F28C 3/08 |
| 2021/0261216 A1* | 8/2021 | Bailar | B62K 3/002 |

* cited by examiner

THREE-DIMENSIONAL STRUCTURE HEATING UNIT AND LIQUID GUIDING UNIT FOR ATOMIZER OF AN E-CIGARETTE

CROSS-REFERENCE APPLICATIONS

This application claims priority to, and incorporates herein in their entireties, Chinese Patent Application No. 201810961311.2 of Aug. 22, 2018, Chinese Patent Application No. 201910048577.2 of Jan. 18, 2019, Chinese Utility Model Application No. 201821963045.9 of Nov. 27, 2018, and Chinese Patent Application No. 201910535711.1 of Jun. 20, 2019.

TECHNICAL FIELD

The present invention relates to an e-cigarette atomizer heating component and liquid conducting component and manufacturing methods thereof, and an atomizer and an e-cigarette with these components, and more particularly to a 3D (three-dimensional) structure heating component and liquid conducting component for e-cigarette atomization generating devices and manufacturing methods thereof, an atomization generating device with these 3D (three-dimensional) structure component, and an e-cigarette with the atomization generating device.

BACKGROUND

An e-cigarette currently used mainly includes an atomizer, a liquid storage tank, a circuit board, and a battery. The liquid storage tank provides an e-liquid for the atomizer, the battery is connected to the circuit board, the circuit board is connected to the atomizer, the battery provides power for the operation of the atomizer, and the circuit board adjusts the operating state of the atomizer.

At present, the atomizing core commonly used in the market is composed of a liquid conducting cotton and a heating wire, that is, the heating wire and the liquid conducting cotton are wound together. When in use, the liquid conducting cotton adsorbs the e-liquid in the liquid storage tank, the heating wire is power-on, and the heating wire generates heat, such that the e-liquid adsorbed by the liquid conducting cotton is heated and atomized.

While the heating wire is energized to heat and atomizes the e-liquid, it is inevitable to heat the liquid conducting cotton near the heating wire. After continuous heating for a long time, the liquid conducting cotton near the heating wire is burned by the heating wire, and the liquid conducting cotton at the position away from the heating wire is still good, which causes partial damage of the liquid conducting cotton. This leads to local damage of the liquid conducting cotton, which in turn results in dry burning of the heating wire and seriously affects the taste of the e-cigarette. When used for a long time, the heating wire is aged, and the adsorption capacity of the liquid conducting cotton is lowered, resulting in poor taste of the e-liquid after atomization. Furthermore, since the e-liquid adsorbed by the liquid conducting cotton is fixed and the operating power of the heating wire is generally constant, it will cause a big problem in the liquid supply of the liquid conducting cotton. In addition, if it is desired to increase the power of atomization, it is necessary to increase heating wires, and winding a plurality of heating wires together easily causes the dry burning such that the liquid conducting cotton is burnt.

Meanwhile, the forming process of liquid conducting cotton commonly used in the market generally adopts a pressure forming method. Fluffy cotton is extruded to a certain shape, such as a cylindrical shape, and then the heating wire is wound in the liquid conducting cotton. The role of the liquid conducting cotton is to guide the e-liquid from a liquid cup into an atomizing zone (heating wire or heating sheet) during operation and to keep the e-liquid in the liquid cup to avoid leakage when not in operation. Therefore, the performance of the liquid conducting cotton is very important. If the liquid conducting cotton is too loose, it will cause liquid leakage. If the liquid conducting cotton is too tight, the liquid supply is insufficient, and this will lead to local dry burning of the heating wire in the atomizing zone, thereby burning the cotton, even directly burning the atomizing core, directly affecting the service life of the atomizing core. The current liquid conducting cotton generally has the following problems:

1. The liquid conducting cotton is too tight, that is, when the liquid conducting cotton is extruded, the cotton is too tight. Although there is no leakage when not in operation, it is easy to cause local dry burning due to insufficient liquid conducting when in continuous operation, which directly affects the service life of the atomizing core.

2. In order to pursue smooth liquid conducting, the liquid conducting cotton is too loose during winding. At this time, the liquid conducting cotton is excessively supplied with the liquid, causing liquid injection of the atomizing core during use or liquid leakage when in a non-operating state.

Therefore, in view of the above problems, it is urgent to redesign an atomizing core component to obtain a novel atomizing core, thereby effectively improving the taste of using e-cigarettes and truly enhancing the user satisfaction of the e-cigarettes.

In view of the above problems, it is necessary to further improve the atomizing core to enhance the taste and user satisfaction. which can be realised by designing a new atomizing core heating component to effectively prevent local overheating, charring and other poor heating phenomena, and/or realised by designing a new atomizing core liquid conducting component to solve the problems of poor liquid supply such as insufficient liquid supply and excessive liquid supply.

SUMMARY

In view of the phenomena of poor heating and poor liquid supply, the present invention provides a three-dimensional structure heating component and 3D (three-dimensional) structure liquid conducting component with a plurality of 3D (three-dimensional) structure units forming a regular convex-concave pattern, and an atomizing core with the three-dimensional structure heating component and/or three-dimensional structure liquid conducting component and an e-cigarette with the atomizing core. The above three-dimensional structure may be simply referred to as 3D.

One of the objects of the present invention is to overcome the defects of poor heating and liquid supply in the prior art, and to provide a 3D heating component for e-cigarettes and a manufacturing method thereof. The heating component is used for guiding, heating and atomizing e-liquid, and has the characteristics of novel design, anti-dry burning, adjustable power at any time, improved liquid supply and delicate taste.

The 3D heating component includes a plate body having upper and lower surfaces, and the plate body is provided with a plurality of 3D heating units for guiding, heating and atomizing the e-liquid. Each of the 3D heating units includes a through hole disposed in the plate body and guide channels distributed regularly at the periphery of the through hole, the through hole runs through the upper and lower surfaces of the plate body, and the guide channels are recessed from the surface of the plate body and communicate with the through hole. The guide channels of the adjacent 3D heating units are connected with each other on the surface of the plate body, and the plurality of 3D heating units form a regular convex-concave pattern on the surface of the plate body.

By disposing the plurality of 3D heating units forming the regular 3D convex-concave pattern on the plate body, the guiding, heating and atomizing area can be effectively and uniformly increased. At the same time, the plurality of recessed guide channels regularly distributed in the convex-concave pattern and the through holes that communicate with the guide channels and are regularly distributed on the surface of the plate body can effectively guide, heat and atomize the fluid, and ensure the large-flow smoke supply, thereby effectively enhancing the user experience.

When the 3D guiding and atomizing heating sheet provided by the present invention is in use, the guide channels can continuously supply the liquid. The molecular force between the e-liquid molecules can be destroyed by the guide channels, so that the atomized e-liquid has delicate and good taste. The plate body can be continuously heated to atomize the e-liquid, and the atomized e-liquid is carried away by the outside air through the through holes, thereby realising large heating area as well as the demand of large amount of smoke, preventing dry burning, effectively improving the problem of liquid supply, and realising integration of liquid supply and atomization.

Further, main liquid passages are further recessed from the upper surface of the plate body or the lower surface of the plate body, and the main liquid passages communicate with the guide channels. Further, the guide channels are grooves or potholes recessed from the upper surface or the lower surface of the plate body, and the grooves re in elongated form. Further, the grooves include grooves distributed horizontally and grooves distributed vertically, and the through holes are located at the intersection of the grooves distributed horizontally and the grooves distributed vertically. Further, the guide channels are potholes recessed from the upper surface or the lower surface of the plate body, and the potholes are circular. Further, the plate body is a metal plate body, and the plate body has a flat plate shape.

Preferably, the 3D heating component for the e-cigarette atomizer may be a 3D grid-like heating sheet, including:

A heating sheet body corresponding to the plate body, where the heating sheet body is provided with a plurality of 3D heating unit groups connected in parallel, and each 3D heating unit group is formed by connecting a plurality of 3D heating units and has a center line. Each 3D heating unit is regularly distributed with a plurality of first through holes along the center line, and a plurality of second through holes are regularly disposed between the center lines of the adjacent 3D heating unit groups. The cross-sectional area of a connecting portion between the first through holes and the adjacent second through holes on the two sides of the center line is equal, the connecting portions are recessed from the surface of the sheet body to form the guide channels, the guide channels communicate with the first through holes and the adjacent second through holes, and the plurality of 3D heating unit groups form a grid-like regular convex-concave pattern on the surface of the sheet body.

Further, each 3D heating unit group, referred to as a 3D unit group, has a first end, a second end, a third end, and a fourth end. The first end and the second end are oppositely disposed, and the third end and the fourth end are oppositely disposed. The first end is used to connect one electrode of the power source, the second end is used to connect another electrode of the power source, and first groove, that is, the first through holes, run through the position of the center line of the heating unit group. The third end is provided with third grooves at a position toward the center line of the heating unit, and the fourth end is provided with fourth grooves at a position toward the center line of the heating unit. The third and fourth grooves correspond to the second through holes.

First connecting sections are formed between the first grooves and the third grooves, second connecting sections is formed between the first grooves and the fourth grooves, and the cross-sectional area of the first connecting sections is equal to the cross-sectional area of the second connecting sections.

Further, two adjacent third grooves in each 3D heating unit group are connected by a third connecting section, two adjacent fourth grooves in each 3D heating unit are connected by a fourth connecting section, and the third grooves and the fourth grooves adjacent in each heating unit group are connected by fifth connecting sections.

The first groove is in the shape of a parallelogram, and the third groove and the fourth groove are both octagonal. The first connecting section is formed of one side of the quadrilateral and one side of the octagonal third groove adjacent thereto, and the second connecting section is formed of another side of the quadrilateral and one side of the octagonal fourth groove adjacent thereto.

The plurality of heating units of the 3D heating component are horizontally disposed, and the upper surface of the heating unit has a flat plate shape. Third protruding portions protrude from a lower surface of the third connecting sections, fourth protruding portions protrude from a lower surface of the fourth connecting sections, and fifth protruding portions protrudes from a lower surface of the fifth connecting section.

Further, a lower surface of the first connecting section, a side surface of the third protruding portion and a side surface of the fifth protruding portion form a first hollow slot, a lower surface of the second connecting section, a side surface of the fourth protruding portion and a side surface of the fifth protruding portion form a second hollow slot, and the first and second hollow slots correspond to the guide channels.

According to the present invention, the cross-sectional area of the first connecting section is equal to the cross-sectional area of the second connecting section. The current enters through the fifth connecting section, equally flows through the first connecting section and the second connecting section, and then continues to flow forward, and the above process is repeated to form a uniform heating circuit. The heating units formed as such have the same heating amount, and the heating is more uniform. The first groove runs through the position of the center line of the heating unit, the third end is provided with the third groove at the position toward the center line of the heating unit, and the fourth end is provided with the fourth groove at the position toward the center line of the heating unit. The heat generated by the heating unit is taken out by the air through the first groove, the third groove and the fourth groove in time, so the taste is more uniform, the heating amount is large and uniform, and the heating is faster.

As a simplified design, the guiding and atomizing heating component can replace the liquid conducting cotton and the heating wire of the conventional atomizing core, and has the functions of liquid conducting and atomization. When the guiding and atomizing heating sheet is energized for heating, the heating area can be greatly increased, the surface contact with the e-liquid is realized, the atomizing and contact area of the e-liquid is greatly enhanced, the e-liquid is atomized more sufficiently, and the amount of e-liquid atomized per unit time is increased, so the component is suitable for lung inhalation. At the same time, the design of the guide channel improves the supply of e-liquid, prevents dry burning, and converts the e-liquid into small molecules, so that the atomized e-liquid has more delicate and better taste.

In order to further enhance the liquid conducting efficiency, the 3D guiding and atomizing heating component with the regularly distributed convex-concave pattern can be combined with different types of e-liquid conducting components, that is, liquid conducting components, to form a relatively complicated atomizing core for e-cigarettes.

For example, in order to further comprehensively enhance the atomization efficiency, the 3D heating component with the regularly distributed convex-concave pattern can be made into a sheet and the liquid conducting component with good liquid conducting effect into a novel atomizing core, for example, made into a 3D component-based ceramic atomizing core with a porous or polycrystalline ceramic liquid conducting body with a grain structure, thereby achieving the comprehensive purposes of realising uniform heat conduction and stable liquid supply, improving the taste of the e-cigarette and enhancing the user satisfaction.

The above grain structure generally refers to a porous material formed after sintering of a mineral or any other material solid (mineral matter) with open pores (the pore shape is basically regular, the shape of the material between the pores is irregular) communicating two opposite surfaces or a polycrystalline (the crystal form is basically regular, the shape of intergranular voids is irregular) material or formed after sintering recrystallization. For the sake of convenience, the liquid conducting material made of the above porous material formed after sintering or the polycrystalline material formed after sintering recrystallization is collectively referred to as a porous ceramic.

At the same time, the 3D heating component can be formed into a grid shape by adjusting the number and distribution rule of the 3D heating units of the 3D heating component provided by the present invention, hereinafter referred to as a grid-like 3D heating component.

One of the objects of the present invention is to provide a ceramic atomizing core based on the grid-like 3D heating component, which has the characteristics of uniform heat, fast heat conduction, large contact area and good taste.

The object of the present invention is achieved in the following way:

An atomizing core based on a porous ceramic liquid conducting component and a grid structure 3D heating component includes: a porous ceramic member having a vent groove, the porous ceramic member having a hollow cylinder shape; and a sheet grid-like 3D heating member, the 3D heating member being provided with a plurality of through holes in a grid shape, and the heating member being disposed on an inner wall of the vent groove of the ceramic liquid conducting component.

Further, the 3D heating member has a heating body, the heating body has a first end surface and a second end surface oppositely disposed, and the through holes are located between the first end surface and the second end surface and run through the heating body. Further, the first end surface is connected to a first pin, the second end surface is connected to a second pin, and the first and second pins are respectively used to be connected to the cathode and anode of the power source.

Further, the through holes are circular, triangular or polygonal. Further, the inner wall of the vent groove of the ceramic liquid conducting component is provided with a receiving groove, and the sheet heating member is sintered to the receiving groove by high temperature.

Further, the 3D heating member is made of a metal material, the periphery of the heating member is sleeved with an induction coil, and the heating member is located in a varying magnetic field generated by the induction coil. Further, the heating member is bent in a barrel shape in the vent groove.

Through the cooperation of the sheet grid-like 3D heating member and the porous ceramic liquid conducting component, the integrated design of liquid conducting and e-liquid atomization is realized, the e-liquid is continuously supplied in the porous ceramic liquid conducting component, and the heating member is in surface contact with the e-liquid in the porous ceramic liquid conducting component, thereby increasing the contact area between the heating member and the e-liquid, effectively preventing the phenomena of local overheating and charring, greatly enhancing the taste of the e-liquid, and enhancing the atomization efficiency of the e-liquid and the amount of e-liquid atomized per unit time.

For example, in order to comprehensively enhance the heating and liquid conducting effects, the grid-like 3D heating component provided by the invention can be made into a sheet shape and made into an atomizing core with a liquid conducting component having good liquid conducting effect. The liquid conducting component can be made of the same material as the conventional liquid conducting cotton to enhance the cost performance and achieve the comprehensive purposes of realising uniform heat conduction and stable liquid supply, improving the taste of the e-cigarette and enhancing the user satisfaction.

One of the objects of the present invention is to overcome the defect of poor liquid supply in the prior art, and to provide a 3D liquid conducting component with a plurality of 3D liquid conducting units. The liquid conducting member may be made of the same material as the conventional liquid conducting cotton, but has the characteristics of smooth and uniform liquid supply, anti-dry burning and liquid leakage prevention as compared with the liquid conducting component made by the conventional method.

The 3D liquid conducting component includes a body, the body is provided with a plurality of 3D liquid conducting units for conducting e-liquid, each of the 3D liquid conducting units includes a convex portion and a concave portion adjacently disposed, and the plurality of 3D liquid conducting units are connected and distributed on the body to form a convex-concave staggered regular pattern.

By disposing the plurality of 3D liquid conducting units forming a regular convex-concave staggered regular pattern on the body, an effective increase in the adsorption and delivery area of the e-liquid can be uniformly and effectively realised on the entire liquid conducting component, the smooth supply of the e-liquid is surely ensured, and leakage of excess e-liquid can be prevented, thereby effectively enhancing the user experience.

The plurality of 3D liquid conducting units form a first liquid conducting zone and a second liquid conducting zone adjacently disposed on the body, the first liquid conducting zone and the second liquid conducting zone are disposed in parallel, the first liquid conducting zone includes a first convex region and a first concave region adjacently disposed, the second liquid conducting zone includes a second convex region and a second concave region adjacently disposed, the first convex region and the second concave region are connected by a first connecting portion, the first concave region and the second convex region are connected by a second connecting portion, a first tearing opening runs through the first connecting portion, and a second tearing opening runs through the second connecting portion.

The supply of the e-liquid is realised by the first tearing opening and the second tearing opening, and the first liquid conducting zone and the second liquid conducting zone can both adsorb/deliver the e-liquid, thereby in turn ensuring the smooth supply of the e-liquid, and also preventing leakage of excess e-liquid.

Further, the body is horizontally disposed, the first convex region is convex upward, the first concave region is concave downward, the first connecting portion connects the lower part of the first convex region and the upper part of the second concave region, and the first tearing opening runs through the first connecting portion in a horizontal direction. The second convex region is convex upward, the second concave region is concave downward, the second connecting portion connects the upper part of the first concave region and the lower part of the second convex region, and the second tearing opening runs through the second connecting portion in the horizontal direction.

Further, the first convex region and the first concave region are connected by a first adapting portion, the second convex region and the second concave region are connected by a second adapting portion, and the first adapting portion and the second adapting portion are both disposed vertically, or the first adapting portion and the second adapting portion are both disposed obliquely. Further, the first tearing opening is disposed in an extending direction of the first liquid conducting zone, and the second tearing opening is disposed in an extending direction of the second liquid conducting zone.

According to the 3D liquid conducting component provided by the present invention, the first convex region and the second concave region are connected by the first connecting portion, the first concave region and the second convex region are connected by the second connecting portion, the first tearing opening runs through the first connecting portion, and the second tearing opening runs through the second connecting portion. The supply of the e-liquid is realised by the first tearing opening and the second tearing opening, and the first and second liquid conducting zones can both adsorb/deliver the e-liquid, thereby in turn ensuring the smooth supply of the e-liquid, and also preventing leakage of excess e-liquid.

The above 3D guiding and atomizing heating component and 3D liquid conducting component can be used alone or in combination to form a novel atomizing core for e-cigarettes, thereby overcoming the defects of poor heating and/or poor liquid supply in the prior art, and enhancing the taste of vaping and user experience.

One of the objects of the present invention is to provide an atomizing core based on the 3D heating component and/or the 3D liquid conducting component, which has the characteristics of uniform heat, fast heat conduction, large contact area and good taste.

The object of the present invention is achieved in the following way: an atomizing core based on a 3D component includes: a 3D heating component described above, and/or a 3D liquid conducting component described above, where when the 3D liquid conducting component and the 3D heating component are used in combination, the 3D liquid conducting component is attached to the surface of the 3D heating component.

One of the objects of the present invention further provides an e-cigarette including the atomizing core based on the 3D heating component and/or the 3D liquid conducting component.

In addition, the present invention further provides a manufacturing method of a 3D heating component for an atomizing core of e-cigarettes, including the following steps:

a. providing a plate body. and performing surface treatment; b. forming a plurality of guide channels and a plurality of through holes on the upper surface or the lower surface of the plate body, the through holes running through the upper and lower surfaces of the plate body; and c. taking out the plate body and cleaning the plate body.

The manufacturing method is simple for manufacturing, convenient for mass production and also convenient for mechanised operation.

Further, in step a, the surface treatment of the plate body includes at least cleaning and drying the surface of the plate body.

Further, during the formation of the plurality of guide channels in step b, the plurality of the guide channels are disposed in parallel or staggered, and the method for forming the guide channels includes stamping, etching, lasering, or laser engraving. During the formation of the plurality of through holes in step b, when the plurality of guide channels are parallel, the through holes are distributed inside the guide channels. When the plurality of guide channels are staggered, the through holes are distributed in staggered zones of the plurality of guide channels, and the method for forming the through holes includes stamping, etching, lasering, or laser engraving.

Further, between steps b and c, the manufacturing method further includes forming main liquid passages on the upper surface of the plate body or the lower surface of the plate body. The main liquid passages communicate with the guide channels, and the method for forming the main liquid passage includes stamping, etching, lasering, or laser engraving.

Preferably, in step b, a protective layer is covered on the surface of the plate body. The protective layer includes a plurality of first recesses and a plurality of second recesses. One of the second recesses is surrounded by the plurality of first recesses. Adjoining positions between the first recesses and the second recesses are connected by a first cover film, and the other places are connected by a second cover film. The etching resistance time of the second cover film is greater than the etching resistance time of the first cover film. Then, the plate body covered with the protective layer is placed in an etching solution for etching, and when the plate body at the first recesses and the second recesses is completely etched, the plate body covered by the first cover film is also partially etched and the plate body covered by the second cover film is not etched, the etching is stopped. In step c, the plate body is taken out, the protective layer is removed, and the plate body is cleaned.

Preferably, in step b, one surface of the plate body is coated with a first cover layer. The first cover layer includes a plurality of first etching baths and of second etching baths, the other surface of the plate body is coated with a second cover layer, the second cover layer is provided with a second alignment baths, and the second alignment baths correspond, to the second etching baths. Then, the preformed plate body is placed in the etching solution. The etching solution enters from the second etching baths and the second alignment baths at the same time and etches the plate body, and the etching solution enters from the first etching baths to etch the plate body. After the plate body between the second etching baths and the second alignment baths is etched, the etching is stopped, and at this time, the plate body at the first etching baths is not completely etched. In step c, the plate body is taken out, the cover layer is removed, and the plate body is cleaned.

Preferably, during the formation of the plurality of guide channels in step b, the plate body is coated with a film, and primary etching is performed to obtain first grooves, a third grooves and fourth grooves. During the formation of the plurality of through holes, the surface of the preformed plate body in step b is dried. One surface of the plate body is subjected to patterning, exposure and development, and the plate body is subjected to secondary etching, such that the plate body between the first grooves and the third grooves is partially removed by etching and the plate body between the first grooves and the fourth grooves is partially removed by etching. In step c, the plate body is taken out, the film is removed, and the plate body is cleaned.

Preferably, during the formation of the plurality of guide channels in step b, a photo-etching process is used. The photo-etching time is controlled, such that first grooves, third grooves and fourth grooves are obtained on the plate body. During the formation of the plurality of through holes in step b, the photo-etching time is controlled again, such that the plate body between the first grooves and the third grooves is partially removed and the plate body between the first grooves and the fourth grooves is partially removed.

The present invention provides multiple manufacturing methods which are simple for operation and convenient for mass production.

In addition, the present invention further provides a manufacturing method of a 3D liquid conducting component for e-cigarettes, including the following steps:

a. providing a press seat, the press seat including a first pressing body and a second pressing body oppositely disposed, and the surfaces of the first and second pressing bodies being provided with convex and concave portions matching each other; and b. placing a flat plate-shaped liquid conducting material between the first pressing body and the second pressing body, and extruding the flat plate-shaped liquid conducting material to obtain the 3D liquid conducting component.

Preferably, in step a, the first pressing body and the second pressing body respectively correspond to a first base body and a second base body, the first base body is provided with first regions and second regions adjacently disposed, the first regions and the second regions are disposed in parallel, the first regions and the second regions both extend in the front-rear direction, a plurality of first protruding portions protrude upward from the first regions, and in the first regions, first gaps are formed between the two first protruding portions adjacent in the front-rear direction, and second gaps are formed between the two first protruding portions adjacent in a left-right direction. The second base body is provided with third regions and fourth regions adjacently disposed, the third region and the fourth regions are disposed in parallel, the third regions and the fourth regions both extend in the front-rear direction, a plurality of third protruding portions protrude downward from the third regions, and in the third regions, third gaps are formed between the two third protruding portions adjacent in the front-rear direction, and fourth gaps are formed between the two third protruding portions adjacent in the left-right direction. The first regions match the fourth regions, the second regions match the third regions, the third protruding portion match the second gaps, and the first protruding portion match the fourth gaps. In step b, the first base body and the second base body are brought close to each other, the first protruding portions move upward to extrude the lower surface of the liquid conducting material, the third protruding portions move downward to extrude the upper surface of the liquid conducting material, the first base body and the second base body continue to be close to each other, the left and right sides of the first protruding portion respectively abut against the two third protruding portions adjacent in the left-right direction, the liquid conducting material at the junction of the first protruding portions and the third protruding portions is cut to form an opening, the first protruding portions continue to push the liquid conducting material upward, the third protruding portions continue to push the liquid conducting material downward, and then the liquid conducting material is formed by extrusion. After the liquid conducting material is extruded, the 3D liquid conducting component is obtained. The 3D liquid conducting component includes a body, the body has first liquid conducting zones and second liquid conducting zones adjacently disposed, the first liquid conducting zones and the second liquid conducting zones are disposed in parallel, the first liquid conducting zones and the second liquid conducting zones are staggered up and down, and the junctions of the first liquid conducting zones and the second liquid conducting zones have the opening.

A plurality of second protruding portions protrude upward from the second regions, a plurality of fourth protruding portions protrude upward from the fourth regions, the second protruding portions and the first protruding portions are staggered in the front-rear direction, and a distance interval is formed between the second protruding portions and the first protruding portions in the front-rear direction. The fourth protruding portions and the third protruding portions are staggered in the front-rear direction, and a distance interval is formed between the fourth protruding portions and the third protruding portions in the front-rear direction.

Preferably, in step a, the first pressing body and the second pressing body respectively correspond to a first roller and a second roller, the first roller is provided with first regions and second regions adjacently disposed, the first regions and the second regions are disposed in parallel, the first regions and the second regions are both disposed around the surface of the first roller, a plurality of first protruding portions protrude from the first region, and a first gap is formed between the adjacent two first protruding portions in one first region. The second roller is provided with third regions and fourth regions adjacently disposed, the third regions and the fourth regions are disposed in parallel, the third regions and the fourth regions are both disposed around the surface of the second roller, a plurality of third protruding portions protrude from the third region, a third gap is formed between the adjacent two third protruding portions in one third region, the first regions match the fourth regions, and the second regions match the third regions. In step b, a flat plate-shaped liquid conducting material is placed between the first roller and the second roller, the first roller and/or second roller are/is rotated, the first protruding portions move toward the fourth regions to extrude one surface of the liquid conducting material, the third protruding portions move toward the second regions to extrude the other surface of the liquid conducting material, the left and right sides of the first protruding portion respectively abut against the two third protruding portions adjacent in the left-right direction, the liquid conducting material at the junction of the first protruding portion and the third protruding portion is cut to form an opening, the first roller and/or second roller continue to rotate, the first protruding portions continue to push the liquid conducting material toward the fourth regions, the third protruding portions continues to push the liquid conducting material toward the second regions, the first roller and/or second roller continue to rotate, the first protruding portions are separated from the third protruding portions, and the liquid conducting material is formed by extrusion.

When viewed along the cross section perpendicular to the axial direction of the first roller, the top of the first protruding portions and the first regions are connected by first inclined surfaces. When viewed along the cross section perpendicular to the axial direction of the second roller, the top of the third protruding portions and the third regions are connected by second inclined surfaces. The first inclined surfaces are located at the first gaps, and the second inclined surfaces are located at the third gaps.

The manufacturing method of the 3D liquid conducting component provided by the present invention is simple in manufacturing process, convenient to operate, and convenient for mass production.

BRIEF DESCRIPTION OF THE DRAWINGS

In order to more clearly illustrate the embodiments of the present invention or the technical solutions in the prior art, the drawings used in the description of the embodiments will be briefly described below. Obviously, the drawings in the following description are only some embodiments of the present invention, and those skilled in the art can obtain other drawings according to these drawings without any creative work.

DETAILED DESCRIPTION

Figure 1:
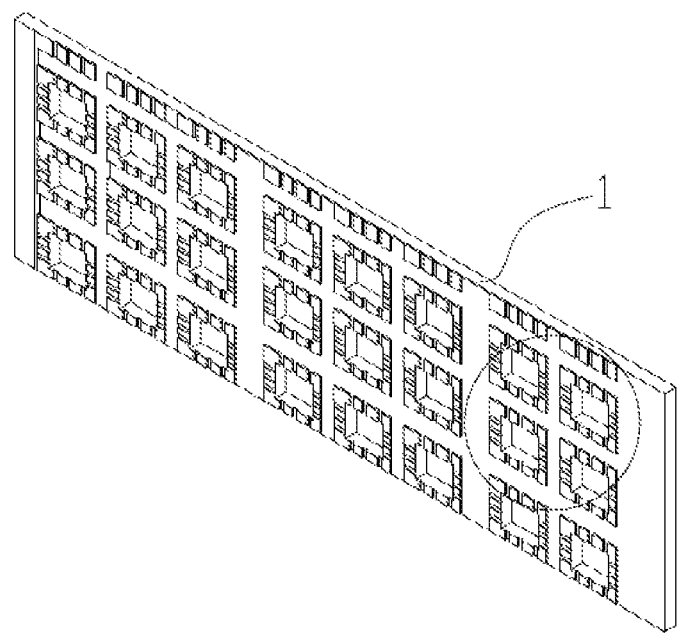
FIG. 1 is an overall 3D (three-dimensional) view of a 3D guiding and atomizing heating component according to the present invention.
Figure 2:
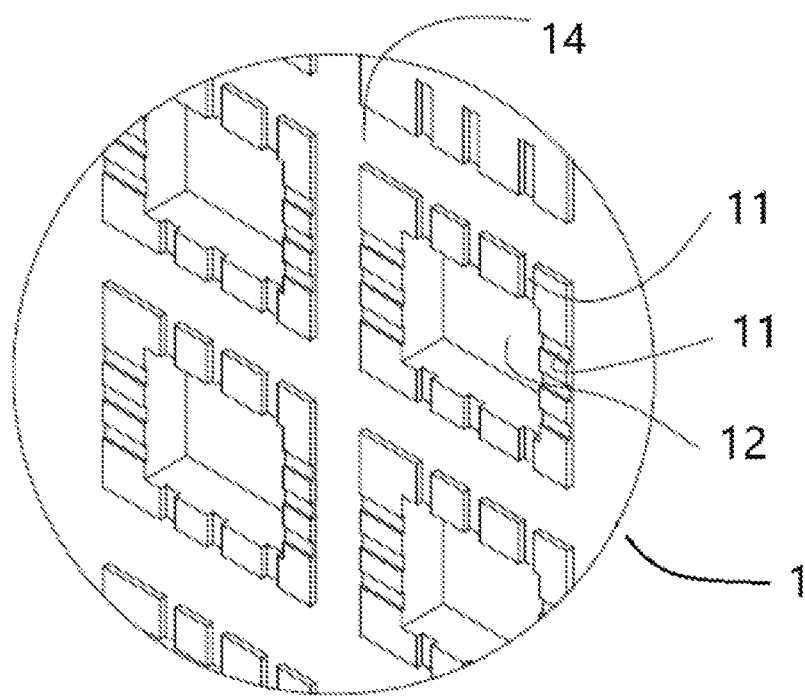
FIG. 2 is a partial enlarged view of FIG. 1 according to the present invention.
Figure 3:
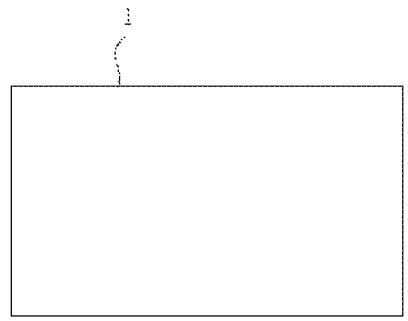
FIG. 3 is a schematic view of a plate body according to the present invention.
Figure 4:
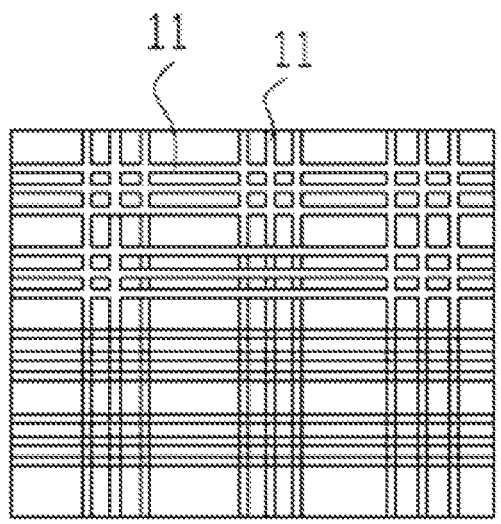
FIG. 4 is a schematic view of guide channels formed in the plate body according to the present invention.
Figure 5:
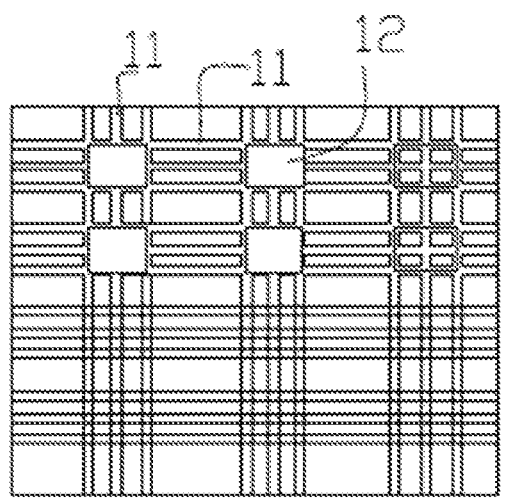
FIG. 5 is a schematic view of guide channels and through holes formed in the plate body according to the present invention.
Figure 6:
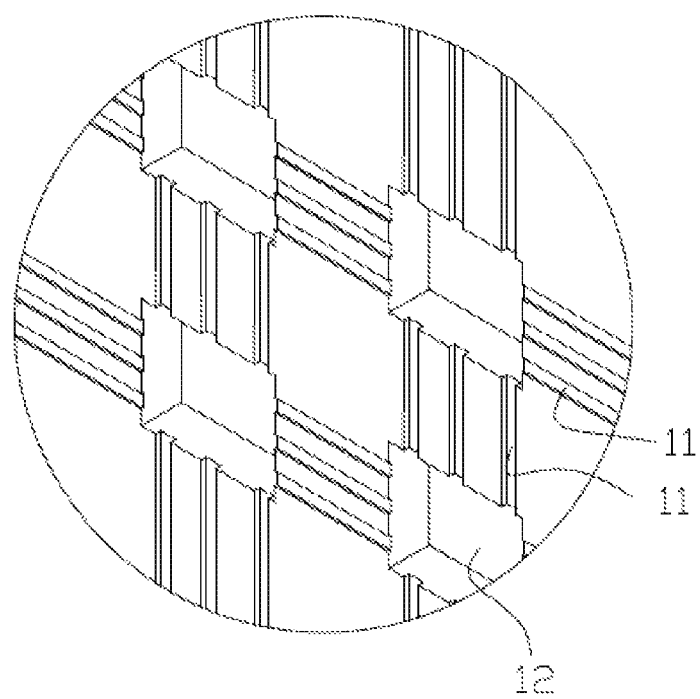
FIG. 6 is an enlarged schematic view of a second embodiment of a 3D guiding and atomizing heating component according to the present invention.

The technical solutions of the present invention will be clearly and completely described below with reference to the drawings in the embodiments of the present invention. It is apparent that the described embodiments are only a part of the embodiments of the present invention, rather than all of the embodiments. All other embodiments obtained by those of ordinary skill in the art based on the embodiments of the present invention without creative work are within the protection scope of the present invention.

As shown in FIG. 1 to FIG. 7, the present invention provides a 3D heating component with a plurality of 3D units forming a regular convex-concave pattern. The 3D heating component may be in the form of a sheet, which may be referred to as a 3D guiding and atomizing heating sheet, and a 3D heating sheet for short.

The 3D heating sheet of the present invention includes a plate body 1, said plate body 1 is provided with a plurality of convex-concave patterns, and regularly distributed 3D heating units for guiding, heating and atomizing the e-liquid. Each of the 3D units is composed of a through hole 12 disposed in the plate body and guide channels 11 distributed regularly at the periphery of the through hole, the through hole runs through the upper and lower surfaces of the plate body, and the guide channels 11 are recessed from the surface of the plate body and communicate with the through hole 12. The guide channels 11 of the adjacent 3D units are connected with each other on the surface of the plate body and form the regular convex-concave pattern on the surface of the plate body.

The plate body 1 is a metal plate body having a certain resistance, also referred to as conductivity. The plate body 1 has a flat plate shape. The plate body 1 is provided with a plurality of guide channels 11 and of through holes 12. The guide channels 11 are recessed from the surface of the plate body 1, the through holes 12 run through the upper and lower surfaces of the plate body 1, and the guide channels 11 communicate with the through holes 12. The guide channels 11 may be interpreted as the function of capillaries. The guide channels 11 may adsorb the e-liquid and destroy the tension on the surface of the e-liquid, so that the e-liquid is converted into small molecules, which facilitates atomization of the e-liquid. At the same time, the capillaries adsorbing the e-liquid can prevent insufficient supply of the e-liquid and effectively prevent the e-liquid from dry burning on the guiding and atomizing heating sheet. A continuous and stable liquid supply is realised by the guide channels 11.

The guide channels 11 are grooves recessed from the upper surface of the plate body 1 or the lower surface of the plate body 1, and the grooves are elongated. The grooves include grooves distributed horizontally and grooves distributed vertically if the plate body is placed vertically, and the through holes 12 are located at the intersection of the grooves distributed horizontally and the grooves distributed vertically. The grooves are similar to capillaries and can adsorb the e-liquid and supply the liquid continuously.

Figure 7:
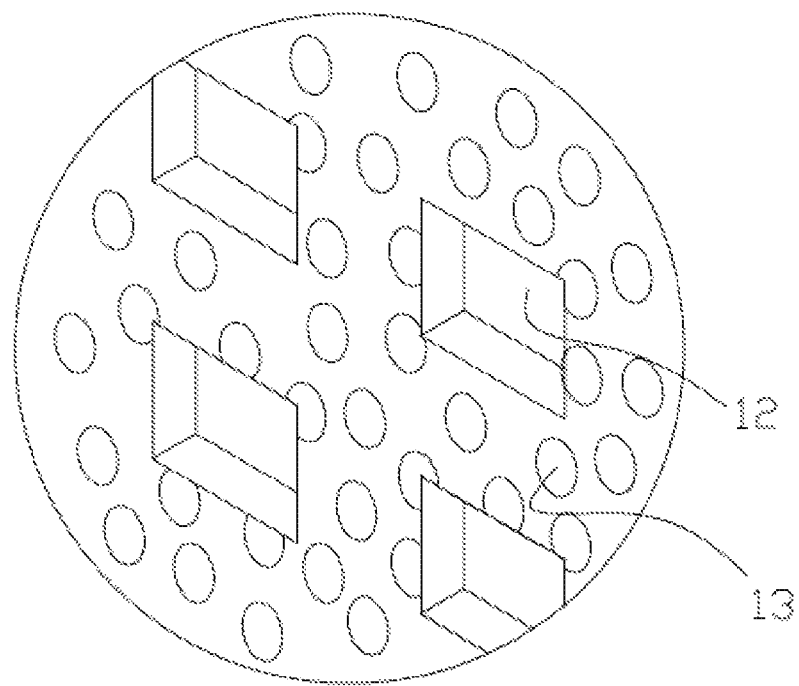
FIG. 7 is an enlarged schematic view of a third embodiment of a 3D guiding and atomizing heating component according to the present invention.

As shown in FIG. 7 the guide channels 11 may also be a depression or a pothole 13 recessed from the upper surface of the plate body 1 or the lower surface of the plate body 1, and the depression 13 is circular. The depression 13 is recessed inward to a certain depth, but does not run through the plate body 1. The adjacent depressions may convert the e-liquid into small molecules through the adsorption of the capillaries, which facilitates the continuous supply and flow of the e-liquid. The principle of liquid supply of the depressions 13 is the same as that of liquid supply, liquid adsorption and liquid conducting of the capillaries, and will not be repeated here again.

Main liquid passages 14 are further recessed from the upper surface of the plate body 1 or the lower surface of the plate body 1, and the main liquid passages 14 communicate with the guide channels 11. The main liquid passages 14 may provide the supply of the e-liquid, and then the e-liquid in the main liquid passages 14 flows into the guide channels 11. Specifically, the guide channels 11 adsorb the e-liquid in the main liquid passages 14 due to the adsorption function, thereby realising continuous liquid supply. The plurality of main liquid passages 14 and the plurality of adjacent 3D units further form a regular convex-concave pattern on the surface of the plate body.

When in use, the e-liquid enters the guiding and atomizing heating sheet through the adsorption function of the guide channels 11, and the adsorption of the e-liquid is realised. After the e-liquid is atomized by the atomizing heating sheet, and the atomized e-liquid is volatilized through the through holes 12. The outside air volatilizes the atomized e-liquid through the through holes 12, the e-liquid is continuously consumed, and the guide channels 11 continuously adsorb the e-liquid and continuously supply the e-liquid, thereby achieving continuous liquid supply. The guiding and atomizing heating sheet replaces the liquid conducting cotton and the heating wire, and has the functions of liquid conducting and atomization. When the guiding and atomizing heating sheet is energized for heating, the heating area can be greatly increased, the surface contact with the e-liquid is realized, the atomizing and contact area of the e-liquid is greatly enhanced, the e-liquid is atomized more sufficiently, and the amount of e-liquid atomized per unit time is increased, so the heating sheet is suitable for lung inhalation. At the same time, the design of the guide channels 11 improves the supply of e-liquid, prevents dry burning, and converts the e-liquid into small molecules, so that the atomized e-liquid has more delicate and better taste.

A manufacturing method of a 3D heating component provided by the present invention includes the following steps:

a. providing a plate body 1, and performing surface treatment;

b. forming a plurality of guide channels 11 and a plurality of through holes 12 on the upper surface or the lower surface of the plate body 1, the through holes 12 running through the upper and lower surfaces of the plate body; and c. taking out the plate body 1 and cleaning the plate body.

Further, in step a, the surface treatment of the plate body 1 includes at least cleaning and drying the surface of the plate body 1. In step b, when the plurality of the guide channels 11 are disposed in parallel or staggered, the method for forming the guide channels 11 includes stamping, etching, lasering, laser engraving, or the like. When the plurality of guide channels 11 are parallel, the through holes 12 are distributed inside the guide channels 11. When the plurality of guide channels 11 are staggered, the through holes 12 are distributed in staggered zones of the plurality of guide channels 11, and the method for forming the through holes 12 includes stamping, etching, lasering, laser engraving, or the like.

Between steps b and c, the manufacturing method further includes forming main liquid passages 14 on the upper surface or the lower surface of the plate body 1. The main liquid passages 14 communicate with the guide channels 11, and the method for forming the main liquid passages includes stamping, etching, lasering, laser engraving, or the like.

As described above, the 3D heating component can be formed into a grid shape by adjusting the number and distribution rule of the 3D heating units of the 3D heating component provided by the present invention, hereinafter referred to as a grid-like 3D heating component. The technical solutions in the embodiments of the grid-like 3D heating sheet of the 3D heating component of the present invention will be clearly and completely described below with reference to FIG. 8 to FIG. 10 in the embodiment of the present invention.

Figure 8:
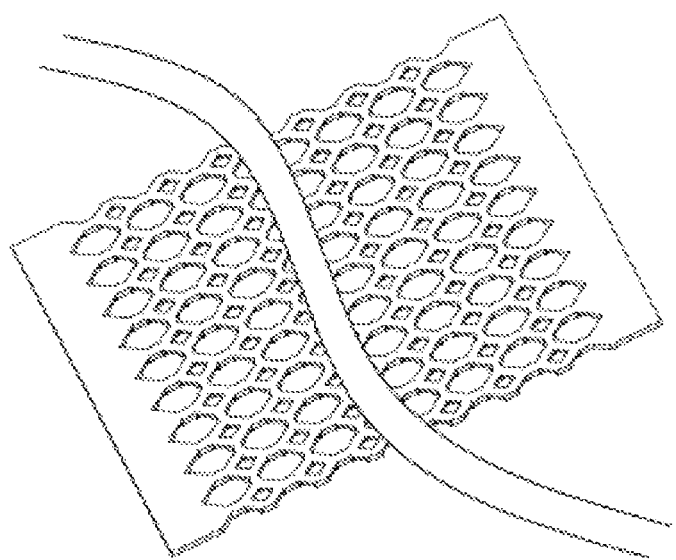
FIG. 8 is a 3D (three-dimensional) view of a grid-like 3D heating component according to the present invention.
Figure 9:
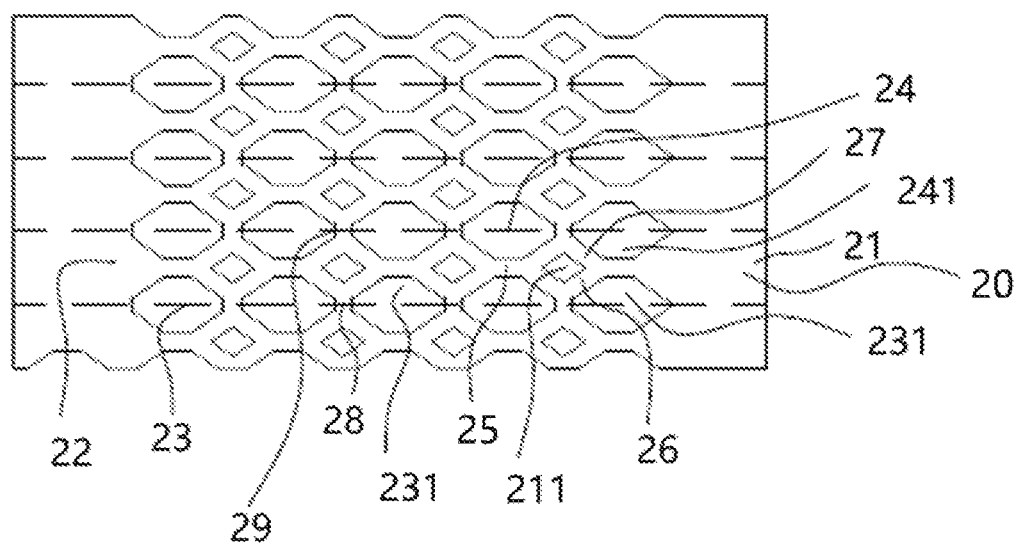
FIG. 9 is a plan view of the grid-like 3D heating component according to the present invention.
Figure 10:
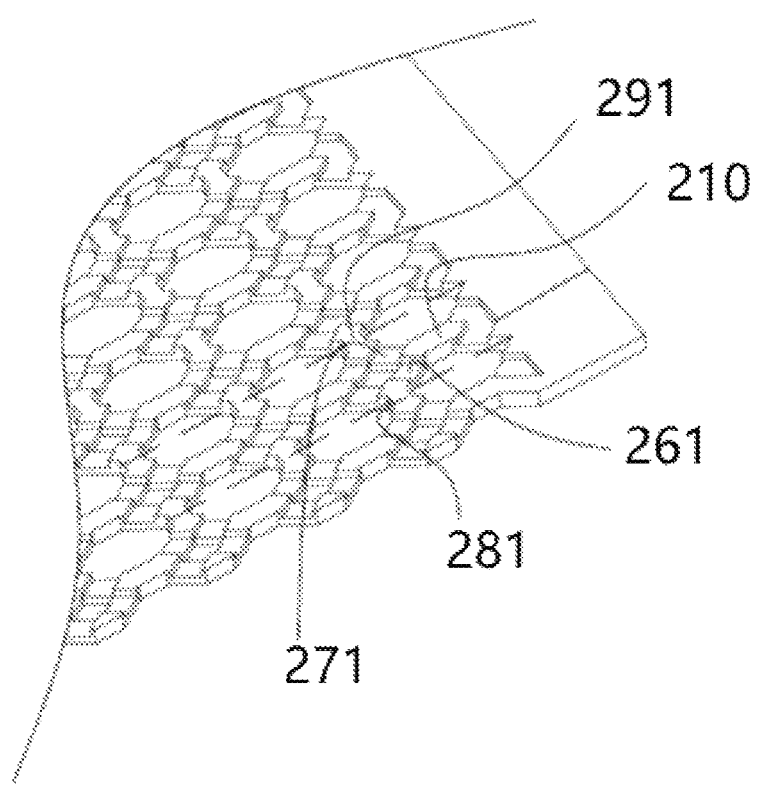
FIG. 10 is a 3D (three-dimensional) view of the grid-like 3D heating component from another viewing angle according to the present invention.
Figure 11:
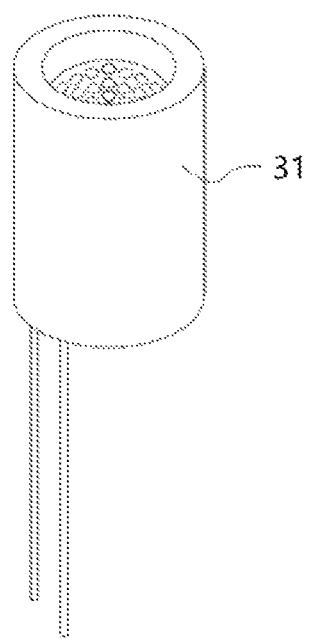
FIG. 11 is an overall view of an atomizing core based on a porous ceramic liquid conducting component and a grid structure 3D heating component according to the present invention.
Figure 12:
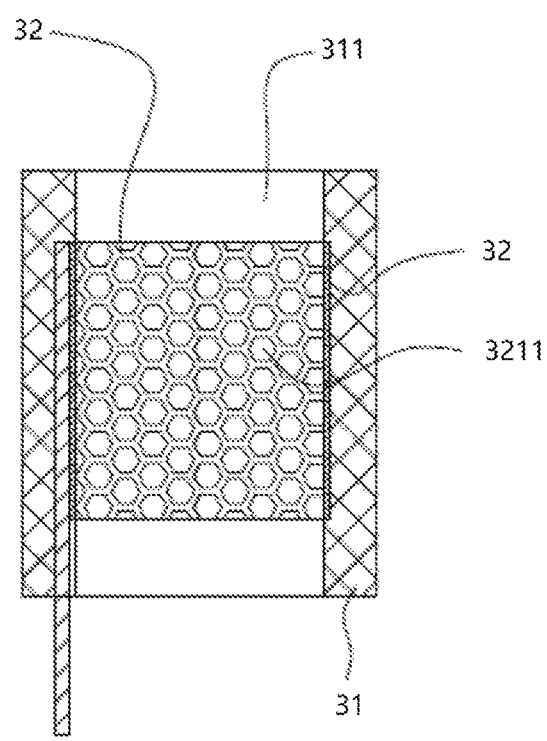
FIG. 12 is an overall cross-sectional view of the atomizing core based on the porous ceramic liquid conducting component and the grid structure 3D heating component according to the present invention.
Figure 13:
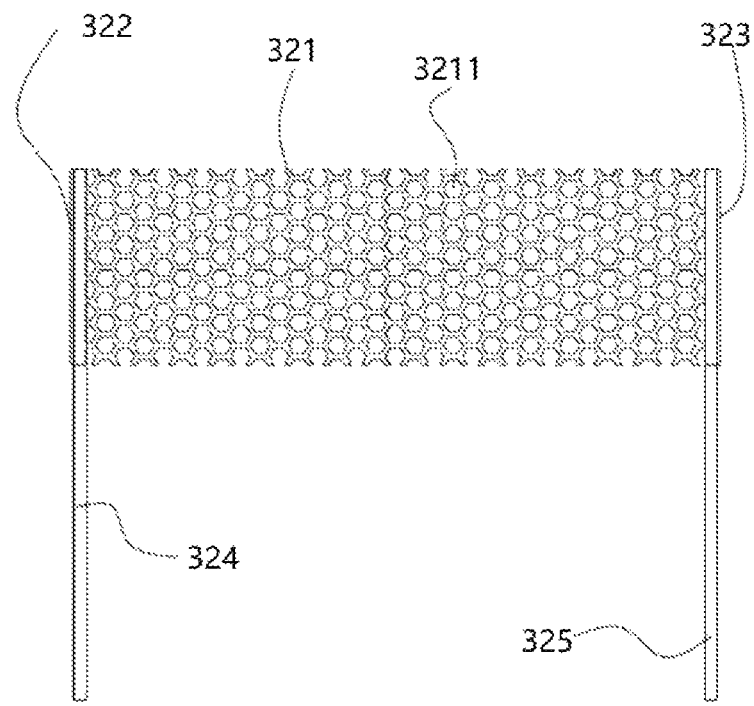
FIG. 13 is a schematic view of an atomizing core heating member based on a porous ceramic liquid conducting component and a grid structure 3D heating component according to the present invention.
Figure 14:
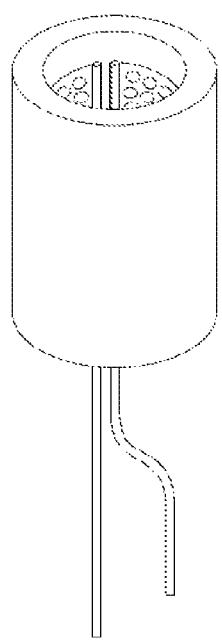
FIG. 14 is a 3D (three-dimensional) view of a second embodiment of an atomizing core heating member based on a porous ceramic liquid conducting component and a grid structure 3D heating component according to the present invention.
Figure 15:
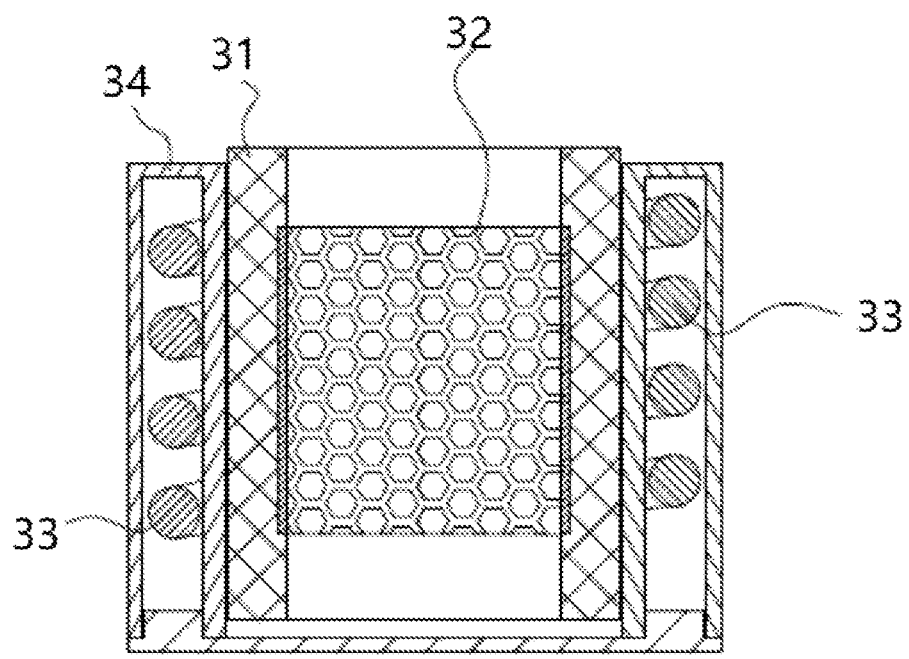
FIG. 15 is a schematic view of electromagnetic induction heating of the second embodiment of the atomizing core heating member based on the porous ceramic liquid conducting component and the grid structure 3D heating component according to the present invention.

As shown in FIG. 8 to FIG. 10, the embodiment of the present invention provides a grid-like 3D heating component, which is often in the form of a sheet and may be referred to as a 3D heating sheet for short. The sheet body is provided with a plurality of 3D heating unit groups connected in parallel, and each 3D heating unit group is formed by linearly connecting a plurality of 3D heating units and has a center line. Each 3D heating unit is regularly distributed with a plurality of first through holes along the center line, and a plurality of second through holes are regularly disposed between the center lines of the adjacent 3D heating unit groups. The cross-sectional area of a connecting portion between the first through hole and the adjacent second through holes on the two sides of the center line is equal, the connecting portions are recessed from the surface of the sheet body to form the guide channels, the guide channels communicate with the first through holes and the adjacent second through holes, and the plurality of 3D heating unit groups form a grid-like regular convex-concave pattern on the surface of the sheet body.

Specifically, each heating unit group 20 in the plurality of 3D heating unit groups disposed in parallel has a first end 21, a second end 22, a third end 23, and a fourth end 24. The first end 21 and the second end 22 are oppositely disposed, and the third end 23 and the fourth end 24 are oppositely disposed. The first end 21 is used to connect one electrode of the power source, the second end 22 is used to connect another electrode of the power source, and first grooves 211, that is, the first through holes, run through the position of the center line of the heating unit group 20. The third end 23 is provided with third grooves 231 at a position toward the center line of the heating unit group, and the fourth end 24 is provided with fourth grooves 241 at a position toward the center line of the heating unit. The third and fourth grooves correspond to the second through holes. First connecting sections 26 are formed between the first grooves 211 and the third grooves 231, second connecting sections 27 are formed between the first grooves 211 and the fourth grooves 241, and the cross-sectional area of the first connecting section 26 is equal to the cross-sectional area of the second connecting section 27.

The adjacent two third grooves 231 in each heating unit group 20 are connected by a third connecting section 28, the adjacent two fourth grooves 241 in each heating unit group are connected by a fourth connecting section 29, and the third groove 231 and fourth groove 241 adjacent in each heating unit group are connected by a fifth connecting section 25.

The first groove, that is the first through hole 211, may be in the shape of a parallelogram, and the third groove 231 and the fourth groove 241, that is, the second through holes, are both octagonal. The first connecting section 26 is formed of one side of the quadrilateral and one side of the octagonal third groove 231 adjacent thereto, and the second connecting section 27 is formed of another side of the quadrilateral and one side of the octagonal fourth groove 241 adjacent thereto.

The heating unit groups 20 are horizontally disposed, and the upper surface of the heating unit groups 20 has a flat plate shape. Third protruding portion 281 protrude from a lower surface of the third connecting sections 28, fourth protruding portions 291 protrude from a lower surface of the fourth connecting sections 29, and fifth protruding portions 210 protrude from a lower surface of the fifth connecting sections 25. The third protruding portions 281 on the lower surface of the third connecting sections 28 may transfer heat generated by the third connecting sections 28, and the fourth protruding portions 291 may transfer heat generated by the fourth connecting sections 29.

A lower surface of the first connecting section 26, a side surface of the third protruding portion 281 and a side surface of the fifth protruding portion 210 form a first hollow slot 261, a lower surface of the second connecting section 27, a side surface of the fourth protruding portion 291 and a side surface of the fifth protruding portion 210 form a second hollow slot 271, and the first hollow slot 261 and the second hollow slot 271 may be used for conducting liquid to facilitate the flow of the e-liquid, and are equivalent to the guide channels. The heat generated by the first connecting section 26 is transferred to the third protruding portion 281, and the heat generated by the second connecting section 27 is transferred to the fourth protruding portion 291, thereby indirectly increasing the heat transfer, increasing the heating area and facilitating the sufficient atomization of the e-liquid. In addition, the fifth protruding portions 210 protrude from a lower surface of the fifth connecting sections 25. The fifth protruding portions 210 may transfer heat generated by the fifth connecting sections 25, thereby increasing the heating area, facilitating the sufficient atomization of the e-liquid and preventing local overheating. Thus, the e-liquid has uniform overall temperature and good taste.

According to the present invention, the cross-sectional area of the first connecting section 26 is equal to the cross-sectional area of the second connecting section 27. The current enters through the fifth connecting sections 25, equally flows through the first connecting sections 26 and the second connecting sections 27, and then continues to flow forward, and the above process is repeated to form a uniform heating circuit. The heating unit group 20 formed as such have the same heating amount, and the heating is more uniform. The first grooves 211 run through the position of the center line of the heating units, the third end 23 is provided with the third grooves 231 at the position toward the center line of the heating unit, and the fourth end 24 is provided with the fourth grooves 241 at the position toward the center line of the heating unit. The heat generated by the heating unit group 20 is taken out by the air through the first grooves 211, the third grooves 231 and the fourth grooves 241 in time, so the taste is more uniform, the heating amount is large and uniform, and the heating is faster. Compared with the conventional heating sheet or heating wire, it has the following advantages:

1. tinder the same power and the same heating area, the grid-like 3D heating sheet has higher heating efficiency and greater explosive power.

2. Under the same conditions, the grid-like 3D heating sheet has a higher temperature, that is, the interval into the mouth is lower, and no higher power is required for driving, which will save energy.

3. tinder the same conditions, due to the large surface area of the grid-like 3D heating sheet, the amount of atomized smoke is larger.

4. Under the same conditions, since the grid like 3D heating sheet has a fine surface texture, the e-liquid will climb up along the fine trenches, the liquid conducting effect is good, and charring cannot easily occur.

A manufacturing process of the grid-like 3D heating sheet of the present invention will be described in detail below, and several methods may be used. The manufacturing process includes the following basic steps:

a. providing a plate body, and performing surface treatment;

b. forming a plurality of guide channels and a plurality of through holes on the upper or lower surface of the plate body, the through holes running through the upper and lower surfaces of the plate body; and c. taking out the plate body and cleaning the plate body.

The first manufacturing method of the 3D heating sheet includes the following steps:

In step a, a substrate is provided, and surface treatment is performed.

In step b, the substrate is preformed firstly, that is, a protective layer is covered on the surface of the substrate. The protective layer includes a plurality of first recesses and a plurality of second recesses. One of the second recesses is surrounded by the plurality of first recesses. Adjoining positions between the first recesses and the second recesses are connected by a first cover film, and the other places are connected by a second cover film. The etching resistance time of the second cover film is greater than the etching resistance time of the first cover film. Then, the substrate is etched, that is, the preformed substrate covered with the protective layer is placed in an etching solution for etching, and when the substrate at the first recesses and the second recesses is completely etched, the substrate covered by the first cover film is also partially etched and the substrate covered by the second cover film is not etched, the etching is stopped.

In step c, the substrate is taken out, the protective layer is removed, and the substrate is cleaned.

Here, it can be simply understood that the etching solution enters the substrate through the second recesses to completely etch the substrate such that the third grooves 231 and the fourth grooves 241 of the 3D heating sheet are formed, and the etching solution enters the substrate through the first recesses to completely etch the substrate such that the first grooves 211 of the 3D heating sheet are formed, and the substrate covered by the first cover film is partially etched and the substrate covered by the first cover film is not completely etched such that the first hollow slots 261 and the second hollow slots 271 are formed in the substrate. The focus is on the first hollow slots 261 and the second hollow slots 271. The substrate at the first hollow slots 261 and the second hollow slots 271 shall not be completely etched, and the substrate at the first recesses needs to be completely etched, which can be achieved only by reasonable control. The thickness of the second cover film is greater than the thickness of the first cover film. The design of using different thicknesses is just one way. The first cover film is etched, and the second cover film is not etched.

The second manufacturing method of the 3D heating sheet includes the following steps:

In step a, a substrate is provided, and surface treatment is performed.

In step b, the substrate is preformed firstly, that is, one surface of the substrate is coated with a first cover layer. The first cover layer includes a plurality of first etching baths and of second etching baths, the other surface of the substrate is coated with a second cover layer, the second cover layer is provided with second alignment baths, and the second alignment baths correspond to the second etching baths. Then, the substrate is etched, that is the preformed substrate in step b is placed in the etching solution. The etching solution enters from the second etching baths and the second alignment baths at the same time and etches the substrate, and the etching solution enters from the first etching bathes to etch the substrate. After the substrate between the second etching baths and the second alignment baths is etched, the etching is stopped, and at this time, the substrate at the first etching baths is not completely etched.

Explained from the thickness of the substrate, the etching solution simultaneously entering from the second etching baths and the second alignment baths and etching the substrate is equivalent to simultaneously etching the substrate from both sides of the substrate. However, the etching solution enters and etches the substrate only from the first etching baths. The speed of entering the substrate simultaneously from both sides and etching the substrate is twice the speed of entering the substrate from the first etching baths and etching the substrate. Therefore, it is theoretically known that the substrate between the second etching baths and the second alignment baths is etched, and the etching is stopped. At this time, the substrate at the first etching baths is not completely etched, only half of the substrate at the first etching baths is etched, the third groove 231, the fourth groove 241 and the first groove 211 are formed in the places where the substrate is etched, and the substrate is not completely etched to form the first hollow slot 261 and the second hollow slot 271.

The second manufacturing method of the 3D heating sheet includes the following steps:

In step a, a substrate is provided, and surface treatment is performed.

In step b, the substrate is coated with a film firstly, primary etching is performed to obtain first grooves 211, third grooves 231 and fourth grooves 241, and then, the surface of the substrate is dried. Then, one surface of the substrate is subjected to patterning, exposure and development, and the substrate is subjected to secondary etching, such that the substrate between the first grooves 211 and the third grooves 231 is partially etched and the substrate between the first grooves 211 and the fourth grooves 241 is partially etched.

In step c, the substrate is taken out, the film is removed, and the substrate is cleaned.

This belongs to a double etching process. The first grooves 211, the third grooves 231 and the fourth grooves 241 are formed by the primary etching, and these grooves act similarly to the previous through holes. Then, etching is performed again. The places where etching is not required are protected, such that the first hollow slots 261 and the second hollow slots 271 are obtained. These hollow slots act similarly to the previous guide channels and main liquid passages.

The fourth manufacturing method of the 3D heating sheet includes the following steps:

In step a, a substrate is provided, and surface treatment is performed.

In step b, a photo-etching process is used. The photo-etching time is controlled, such that first grooves 211, third grooves 231 and fourth grooves 241 are obtained on the substrate. The photo-etching time is controlled again, such that the substrate between the first grooves 211 and the third grooves 231 is partially removed and the substrate between the first grooves 211 and the fourth grooves 241 is partially removed.

This process of controlling the depth at which metal on the substrate is removed by photo-etching according to the photo-etching time and photo-etching intensity belongs to a photo-etching process, and needs to be used in conjunction with specially designed software.

The multiple manufacturing methods of the 3D heating sheet provided by the present invention are used for manufacturing the 3D heating sheet. The methods are simple to operate and convenient for mass production.

The technical solutions in the embodiments of the present invention will be clearly and completely described below with reference to the drawings in the embodiment of a ceramic atomizing core based on the grid-like 3D heating component provided by the present invention.

As shown in FIG. 11 to FIG. 15, the embodiment of the present invention provides a ceramic atomizing core based on a porous heating grid, including: a porous ceramic liquid conducting body 31, having a vent groove 311, the porous ceramic liquid conducting body 31 having a hollow cylinder shape; and a 3D heating member 32 in the form of a sheet, the heating member 32 being provided with a plurality of through holes 3211 in a grid shape, and the heating member 32 being disposed on an inner wall of the vent groove 311.

The heating member 32 may be the 3D heating component (3D heating sheet) described above. The heating member 32 has a body 321, the body 321 has a first end surface 322 and a second end surface 323 oppositely disposed, the through holes 3211 run through the body 321, and the through holes 3211 are located between the first end surface 322 and the second end surface 323. The first end surface 322 is connected to a first pin 324, the second end surface 323 is connected to a second pin 325, and the first pin 324 and the second pin 325 are respectively used to be connected to the cathode and anode of the power source. The heating member 32 itself has a certain resistance or impedance, and when a certain current is provided, the heating member generates heat.

The through hole 3211 is circular, triangular, or polygonal, and the polygon includes a quadrilateral, a pentagon, a hexagon, and the like, which will not be enumerated. The heating member 32 is bent into a barrel shape in the vent groove 311 to facilitate the cooperation and shape matching of the heating member 32 with the vent groove 311 in the porous ceramic 31. During the formation, the heating member 32 may be bent into a barrel shape firstly, and then the heating member 32 is placed in the vent groove 311 for high-temperature sintering, which is also called secondary sintering. Since the primary sintering is the sintering of the porous ceramic 31, recrystallization occurs during the primary sintering, and after cooling, the secondary sintering is performed. The inner wall of the vent groove 311 is provided with a receiving groove, and the heating member 32 is sintered to the receiving groove by high temperature.

The heating member 32 is made of a metal material, such as an iron-containing alloy or an iron-containing metal material, the periphery of the heating member 32 is sleeved with an induction coil 33, and the heating member 32 is located in a varying magnetic field generated by the induction coil 33. Specifically, the periphery of the porous ceramic 31 is provided with the induction coil 33, and the induction coil 33 is sleeved on the periphery of the porous ceramic 31. When an alternating current is connected to the induction coil 33, the alternating current generates a varying magnetic field through the induction coil 33, the heating member 32 is placed in the varying magnetic field, and an eddy current is generated in the heating member 32, such that the heating member 32 generates heat and the e-liquid in the porous ceramic 31 is atomized. In this heating method, the heating member 32 has a high heating speed, so a large amount of heat can be generated in an instant to atomize the e-liquid of the porous ceramic 31. A spacer 34 may be added between the induction coil 33 and the porous ceramic 31 to prevent the e-liquid from entering the induction coil 33, thereby ensuring the normal operation of the induction coil 33.

Through the cooperation of the heating member 32 and the porous ceramic 31, the integrated design of liquid conducting and e-liquid atomization is realized, the e-liquid flows in the porous ceramic 31 such that the e-liquid is continuously supplied in the porous ceramic 31, and the heating member 32 is in surface contact with the e-liquid in the porous ceramic 31, thereby increasing the contact area between the heating member 32 and the e-liquid, effectively preventing the phenomena of local overheating and charring, greatly enhancing the taste of the e-liquid, and enhancing the atomization efficiency of the e-liquid and the amount of e-liquid atomized per unit time.

The technical solutions of the 3D liquid conducting component with a plurality of 3D liquid conducting units forming a regular convex-concave pattern in the embodiment of the present invention will be clearly and completely described below with reference to FIG. 16 to FIG. 27 in the embodiment of the present invention.

As shown in FIG. 16 to FIG. 27, the embodiment of the present invention provides a 3D liquid conducting component and a manufacturing method thereof. For details, reference is made to the following description.

Referring to FIG. 17 to FIG. 21, a manufacturing method of a 3D liquid conducting component includes the following steps:

a. providing a press seat, the press seat including first pressing bodies 41, 51 and second pressing bodies 52, 52 oppositely disposed, and the surfaces of the first pressing bodies and of the second pressing bodies being provided with convex and concave portions corresponding to each other; and b. placing a flat plate-shaped liquid conducting material 50 between the first pressing bodies 41, 51 and the second pressing bodies 42, 52, and extruding the flat plate-shaped liquid conducting material 50 to obtain the 3D liquid conducting component.

One of the embodiments includes the following specific steps:

In step a, a press seat is provided. The press seat includes a first base body 41 and a second base body 42 oppositely disposed, the first base body 41 is provided with first regions 411 and second regions 412 adjacently disposed, the first regions 411 and the second regions 412 are disposed in parallel, the first regions 411 and the second regions 412 both extend in the front-rear direction, a plurality of first protruding portions 413 protrude upward from the first region 411, and in the first region 411, first gaps 414 are formed between the two first protruding portions 413 adjacent in the front-rear direction, and second gaps 415 are formed between the two first protruding portions 413 adjacent in a left-right direction. The second base body 42 is provided with third regions 421 and fourth regions 422 adjacently disposed, the third regions 121 and the fourth regions 422 are disposed in parallel, the third regions 421 and the fourth regions 422 both extend in the front-rear direction, a plurality of third protruding portions 423 protrude downward from the third regions 421, and in the third regions 421, a third gap 424 is formed between the two third protruding portions 423 adjacent in the front-rear direction, and a fourth gap 425 is formed between the two third protruding portions 423 adjacent in the left-right direction. The first regions 411 match the fourth regions 422, the second regions 412 match the third regions 421, the third protruding portions 423 match the second gaps 415, and the first protruding portions 413 match the fourth gaps 425.

In step b, a flat plate-shaped liquid conducting material 50 is placed between the first base body 41 and the second base body 42, the first base body 41 and the second base body 42 are brought close to each other, the first protruding portions 413 move upward to extrude the lower surface of the liquid conducting material 50, the third protruding portions 423 move downward to extrude the upper surface of the liquid conducting material 50, the first base body 41 and the second base body 42 continue to be close to each other, the left and right sides of the first protruding portion 413 respectively abut against the two third protruding portions 423 adjacent in the left-right direction, the liquid conducting material 50 at the junction of the first protruding portions 413 and the third protruding portions 423 is cut to form an opening, the first protruding portions 413 continue to push the liquid conducting material 50 upward, the third protruding portions 423 continue to push the liquid conducting material 50 downward, and then the liquid conducting material is formed by extrusion.

A plurality of second protruding portions 416 protrude upward from the second region 412, a plurality of fourth protruding portions 426 protrude upward from the fourth region 422, the second protruding portions 416 and the first protruding portions 413 are staggered in the front-rear direction, and a distance interval is formed between the second protruding portion 416 and the first protruding portion 413 in the front-rear direction. The fourth protruding portions 426 and the third protruding portions 423 are staggered in the front-rear direction, and a distance interval is formed between the fourth protruding portion 426 and the third protruding portion 423 in the front-rear direction.

Referring to FIG. 22 to FIG. 26, a first embodiment of a manufacturing method of a 3D liquid conducting component includes the following specific steps:

In step a, a press seat is provided. The press seat includes a first roller 51 and a second roller 52 oppositely disposed, the first roller 51 is provided with first regions 511 and second regions 512 adjacently disposed, the first regions 511 and the second regions 512 are disposed in parallel, the first regions 511 and the second regions 512 are both disposed around the surface of the first roller 51, a plurality of first protruding portions 513 protrude from the first region 511, and a first gap 514 is formed between the adjacent two first protruding portions 513 in one first region 511. The second roller 52 is provided with third regions 521 and fourth regions 522 adjacently disposed, the third regions 521 and the fourth regions 522 are disposed in parallel, the third regions 521 and the fourth regions 522 are both disposed around the surface of the second roller 52, a plurality of third protruding portions 523 protrude from the third regions 521, a third gap 524 is formed between the adjacent two third protruding portions 523 in one third region 521, the first regions 511 match the fourth regions 522, and the second regions 512 match the third regions 521.

In step b, a flat plate-shaped liquid conducting material 50 is placed between the first roller 51 and the second roller 52, the first roller 51 and/or second roller 52 are/is rotated, the first protruding portions 513 move toward the fourth regions 522 to extrude one surface of the liquid conducting material 50, the third protruding portions 523 move toward the second regions 512 to extrude the other surface of the liquid conducting material 50, the left and right sides of the first protruding portion 513 respectively abut against the two third protruding portions 523 adjacent in the left-right direction, the liquid conducting material 50 at the junction of the first protruding portion 513 and the third protruding portion 523 is cut to form an opening, the first roller 51 and/or second roller 52 continue to rotate, the first protruding portions 513 continue to push the liquid conducting material 50 toward the fourth regions 522, the third protruding portions 523 continue to push the liquid conducting material 50 toward the second regions 512, the first roller 51 and/or second roller 52 continue to rotate, the first protruding portions 513 are separated from the third protruding portions 523, and the liquid conducting material 50 is formed by extrusion.

When viewed along the cross section perpendicular to the axial direction of the first roller 51, the top of the first protruding portion 513 and the first region 511 are connected by a first inclined surface 515. When viewed along the cross section perpendicular to the axial direction of the second roller 52, the top of the third protruding portion 523 and the third region 521 are connected by a second inclined surface 525. The first inclined surface 515 is located at the first gap 514, and the second inclined surface 525 is located at the third gap 524.

Figure 16:
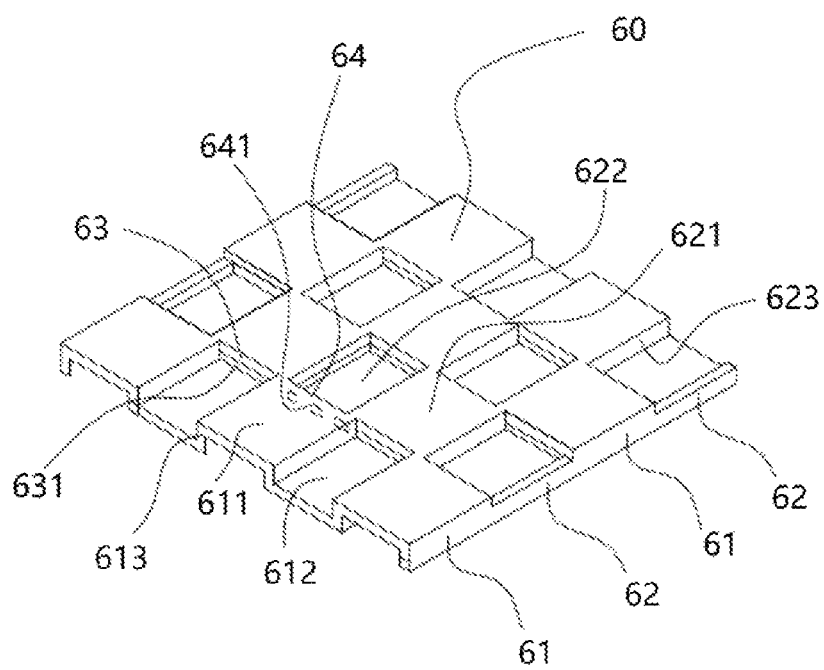
FIG. 16 is a 3D (three-dimensional) view of a 3D liquid conducting component according to the present invention.
Figure 17:
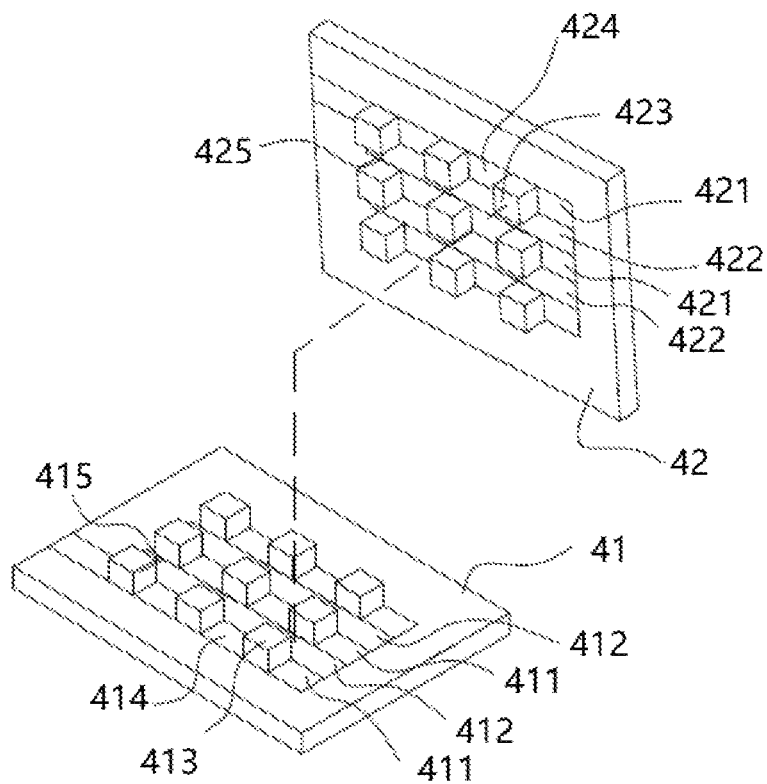
FIG. 17 is a 3D (three-dimensional) exploded view of a first embodiment of pressing bodies for forming the 3D liquid conducting component according to the present invention.
Figure 18:
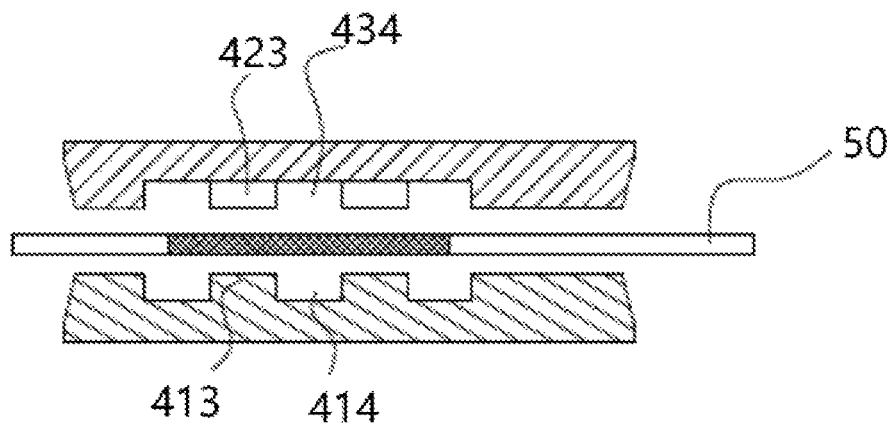
FIG. 18 is a cross-sectional view of a first base body and a second base body of the 3D liquid conducting component according to the present invention.
Figure 19:
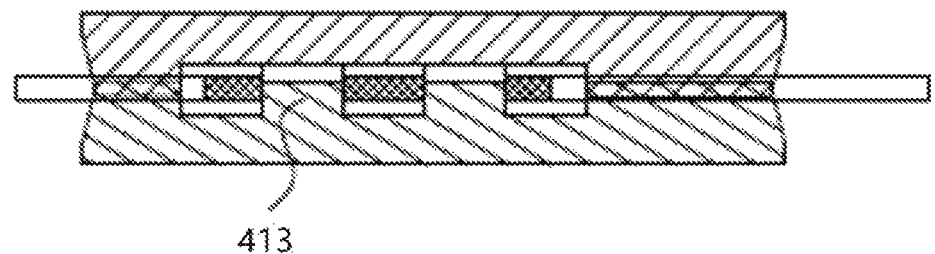
FIG. 19 is a cross-sectional view after the first base body and the second base body of the 3D liquid conducting component are pressed together according to the present invention.
Figure 20:
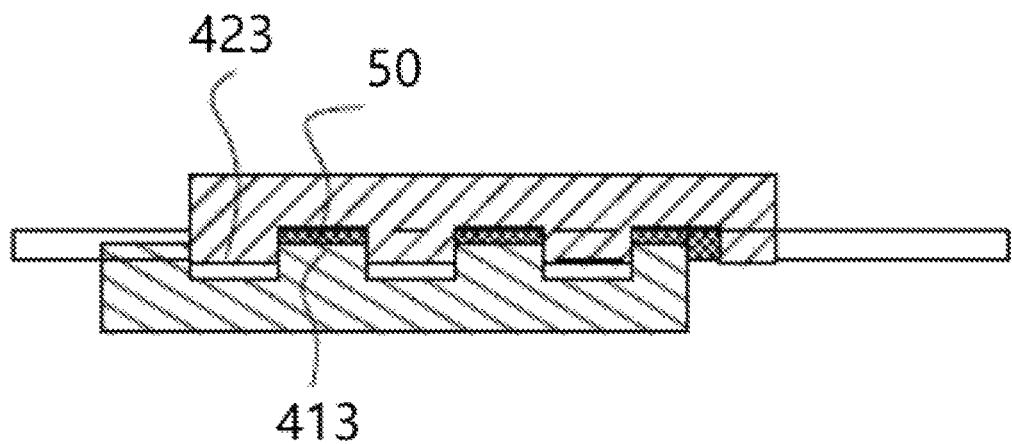
FIG. 20 is a cross-sectional view after the first base body and the second base body of the 3D liquid conducting component are pressed together from another viewing angle according to the present invention.
Figure 21:
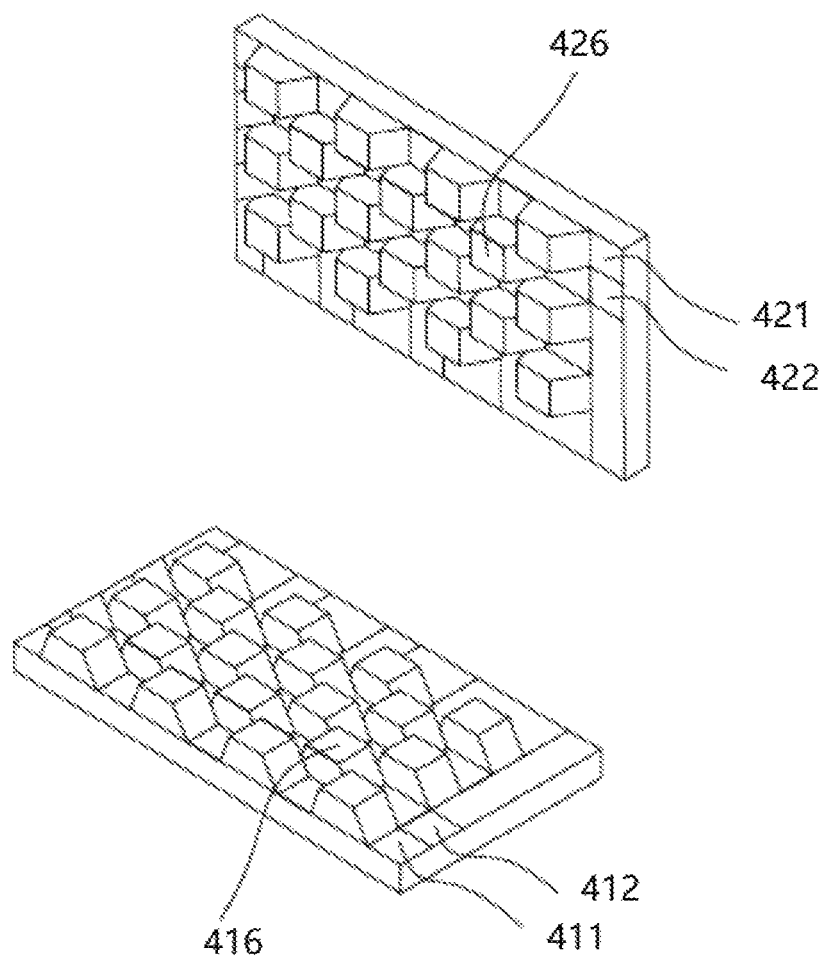
FIG. 21 is a schematic view of a second embodiment of pressing bodies for forming the 3D liquid conducting component according to the present invention.
Figure 22:
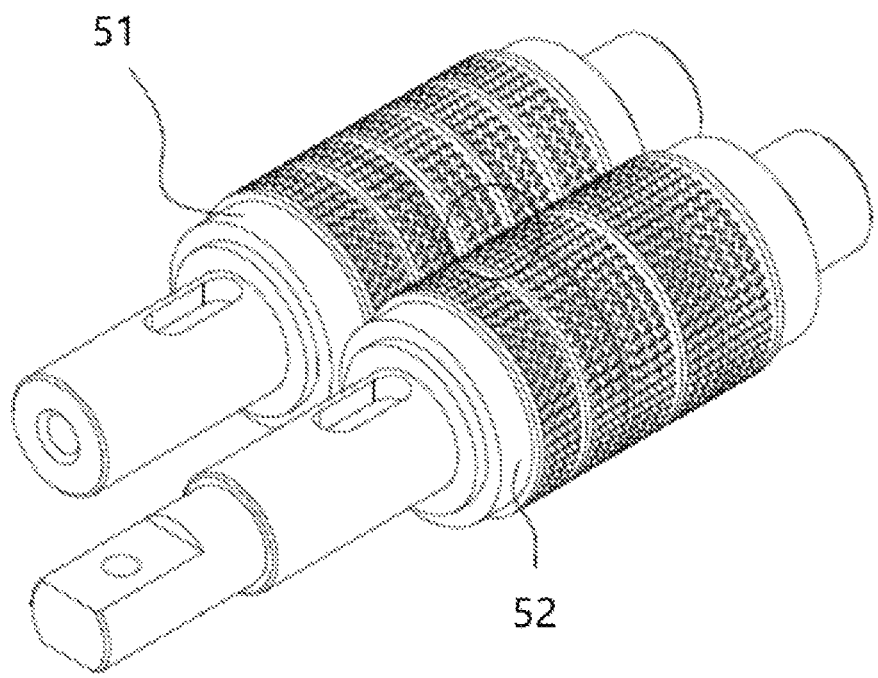
FIG. 22 is a 3D (three-dimensional) view of a third embodiment of pressing bodies for forming the 3D liquid conducting component according to the present invention.
Figure 23:
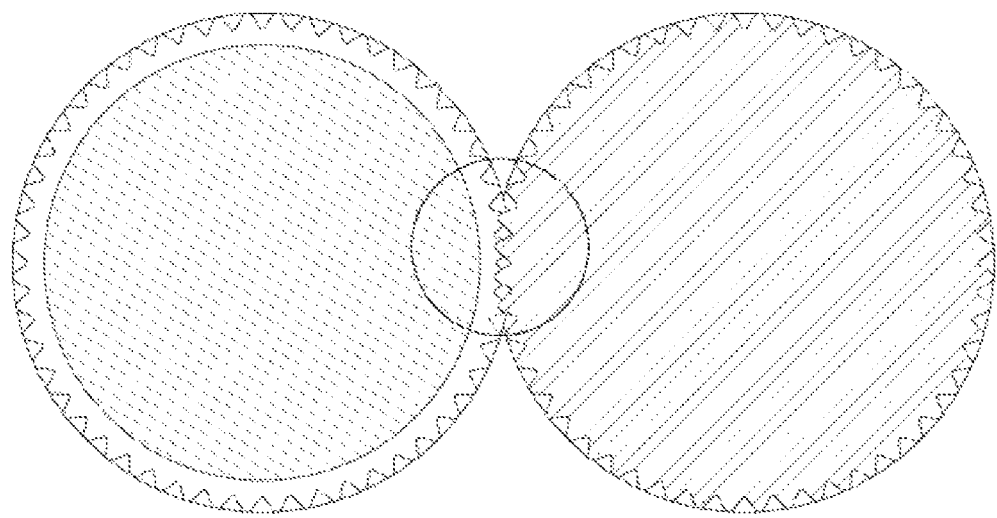
FIG. 23 is a cross-sectional view of the third embodiment of the pressing bodies for forming the 3D liquid conducting component according to the present invention.
Figure 24:
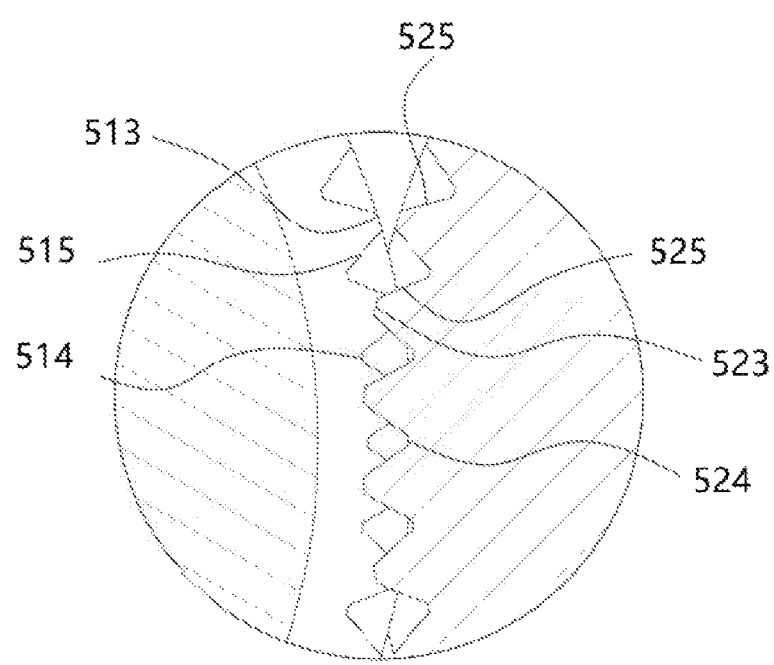
FIG. 24 is a partial enlarged view of FIG. 23 according to the present invention.
Figure 25:
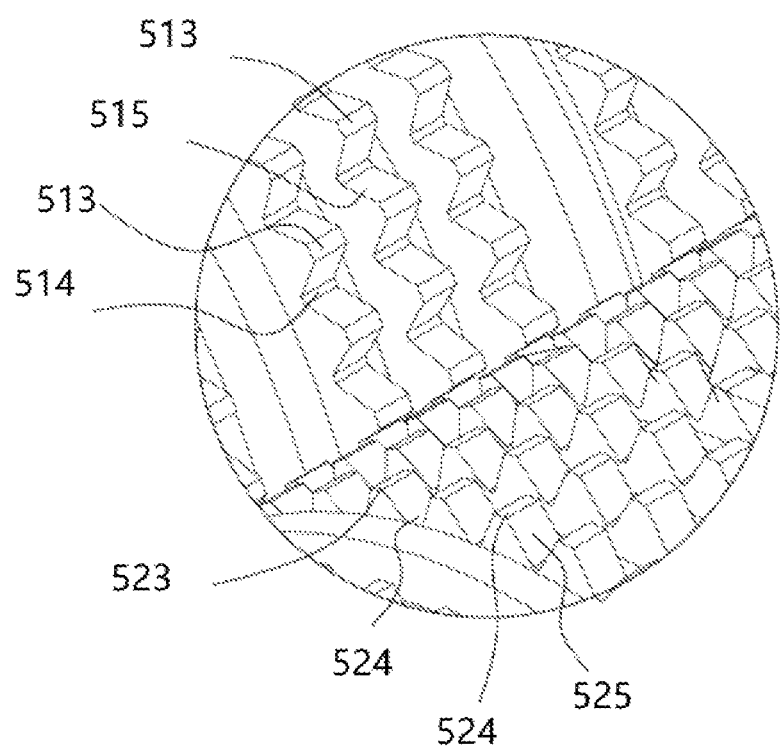
FIG. 25 is a partial enlarged view of FIG. 22 according to the present invention.

Referring to FIG. 16, the present invention provides a 3D liquid conducting component, which is a product formed by using the method provided by the present invention, including: a body 60, a plurality of 3D liquid conducting units disposed on the body (60) being used for conducting e-liquid. Each of the 3D liquid conducting units includes a convex portion and a concave portion adjacently disposed, and the plurality of 3D liquid conducting units are connected and disposed on the body to form a convex-concave staggered regular pattern.

The body 60 has first liquid conducting zones 61 and second liquid conducting zones 62 adjacently disposed, the first liquid conducting zones 61 and the second liquid conducting zones 62 are disposed in parallel, the first liquid conducting zone 61 includes first convex regions 611 and first concave regions 612 adjacently disposed, the second liquid conducting zone 62 includes second convex regions 621 and second concave regions 622 adjacently disposed, the first convex region 611 and the second concave region 622 are connected by a first connecting portion 63, the first concave region 612 and the second convex region 621 are connected by a second connecting portion 64, a first tearing opening 631 runs through the first connecting portion 63, and a second tearing opening 641 runs through the second connecting portion 64. For example, the first tearing opening 631 and the second tearing opening 641 are formed by cutting the liquid conducting material 50 at the junction of the first protruding portion 613 and the third protruding portion 623 to form the opening. When the first protruding portion 613 and the third protruding portion 623 meet, it is equivalent to two cutters, and the liquid conducting material 50 is cut here to form the opening.

For another example, in the second embodiment, the liquid conducting material 50 at the junction of the first protruding portion 513 and the third protruding portion 523 is cut to form the opening, thereby forming the first tearing opening 631 and the second tearing opening 641. The first roller 51 and/or second roller 52 are rotated, the first protruding portions 513 continue to push the liquid conducting material 2 toward the fourth regions 522, and the third protruding portions 523 continue to push the liquid conducting material 50 toward the second regions 512. The first tearing opening 631 and the second tearing opening 641 are stretched vertically and also stretched transversely, the first protruding portions 513 extrude the liquid conducting material 50 downward such that the first concave regions 612 are formed, and the third protruding portions 523 extrude the liquid conducting material 50 upward such that the second convex regions 621 are formed.

The body 60 is horizontally disposed, the first convex regions 611 are convex upward, the first concave regions 612 are concave downward, the first connecting portions 63 connect the lower part of the first convex regions 611 and the upper part of the second concave regions 622, and the first tearing openings 631 run through the first connecting portions 63 in a horizontal direction. The second convex regions 621 are convex upward, the second concave regions 622 are concave downward, the second connecting portions 64 connects the upper part of the first concave regions 612 and the lower part of the second convex regions 621, and the second tearing openings 641 run through the second connecting portions 64 in the horizontal direction.

The first convex region 611 and the first concave region 612 are connected by a first adapting portion 613, the second convex region 621 and the second concave region 622 are connected by a second adapting portion 623, and the first adapting portions 613 and the second adapting portions 623 are both disposed vertically, or the first adapting portions 613 and the second adapting portions 623 are both disposed obliquely. The first tearing openings 631 are disposed in an extending direction of the first liquid conducting zones 61, and the second tearing openings 641 are disposed in an extending direction of the second liquid conducting zones 62.

Figure 26:
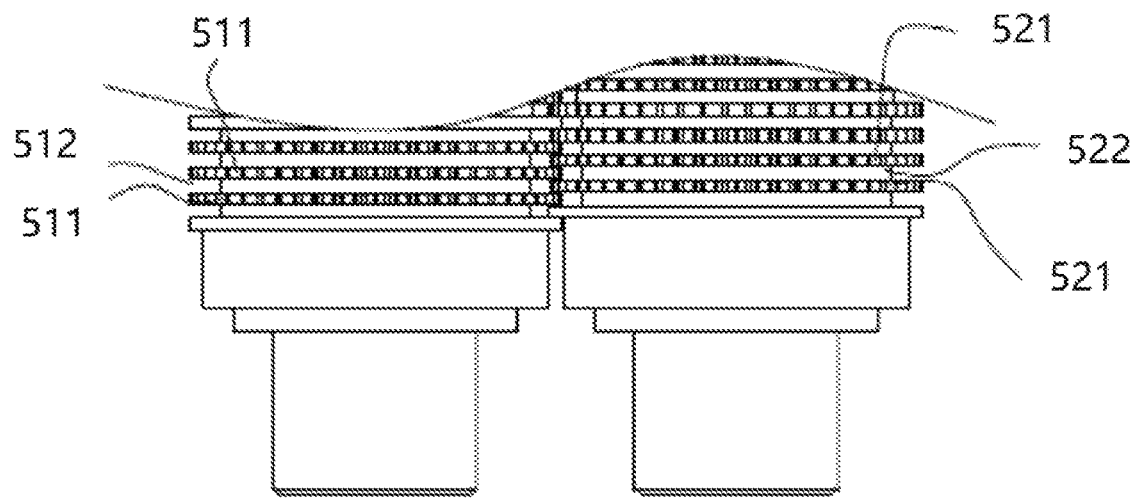
FIG. 26 is a schematic plan view of the third embodiment of the pressing bodies for forming the 3D liquid conducting component according to the present invention.
Figure 27:
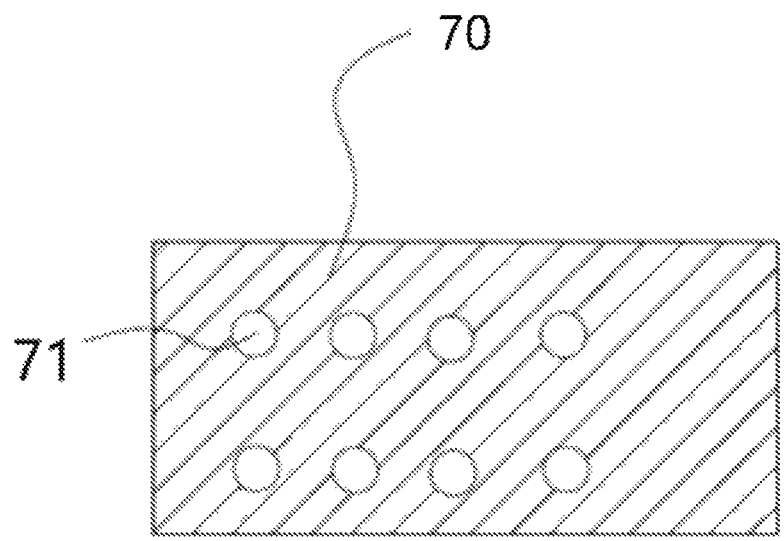
FIG. 27 is a schematic view of a fourth embodiment of pressing bodies for forming the 3D liquid conducting component according to the present invention.

The present invention provides a 3D liquid conducting component, which is a product formed by using the method provided by the present invention. The 3D liquid conducting component is composed of a liquid conducting cotton or a nonwoven fabric. The liquid conducting cotton is subjected to 3D treatment, that is, the liquid conducting cotton is pressed into a three-dimensional/3D pattern by stamping or rolling, which is a 3D structure both inside and outside. Inside the 3D structure, after compaction, the liquid conducting, cotton is also combined with certain gaps (the size and number of which are determined according to the type of the atomizer), in order to increase the liquid storage space. The thickness of the liquid conducting cotton subjected to 3D treatment is greater than the conventional thickness, but the number of the liquid conducting cottons has not changed from the past, and there is only an increase in the three-dimensional effect and certain gaps as well as an increase in the thickness. Thus, the insufficient liquid storage amount of the single opening is avoided, and when the liquid conducting cotton operates after being compacted, it will swell when encountering the e-liquid, so that local dry burning is not easily caused. Although the liquid conducting cotton subjected to 3D treatment is partially compacted after 3D modification, numerous small holes are distributed in the middle to promote smooth liquid supply. The conventional liquid conducting cotton is not provided with liquid conducting openings (that is, the first tearing openings 631 and the second tearing openings 641 provided in the liquid conducting component of the design). The modified liquid conducting cotton can store more e-liquid than the conventional liquid conducting cotton, and has better liquid conducting performance Some contact parts are simply fine holes (that is, the first tearing openings 631 and the second tearing openings 641 provided in the liquid conducting component of the design), and the liquid conducting cotton itself can also supply the liquid, so that good liquid supply can be realised. At the same time, the first liquid conducting zones 61 and the second liquid conducting zones 62 utilize the characteristic of adsorbing e-liquid of the liquid conducting cotton itself, which can contain the e-liquid and store the e-liquid, thereby preventing liquid leakage. Therefore, the 3D liquid conducting component has better performance, and alleviates the contradiction between the two balances. FIG. 26 shows a simple 3D liquid conducting component 70. The principle of the recesses 71 formed in the surface of the liquid conducting material by stamping is similar to that of the above-mentioned 3D liquid conducting component, and will not be described again.

In addition, the liquid conducting cotton subjected to 3D treatment may be combined with the nonwoven fabric. The liquid conducting cotton subjected to 3D treatment has uneven texture and holes both inside and outside, and will be not flat when the heating wire or heating sheet is mounted, so it is necessary to combine a layer of flat nonwoven fabric with the surface near the heating sheet or heating wire. In fact, the conventional liquid conducting cotton is just like this to make the appearance beautiful one the one hand and make it flatter on the other hand. Especially when the heating sheet is used, the liquid conducting cotton is more indispensable, and has a function of preventing liquid leakage of the atomizing core due to the capillary action since some fine cotton threads of the liquid conducting cotton are sometimes attached to the inner wall of the atomizing core.

The above description is only the preferred embodiments of the present invention and is not intended to limit the present invention. Any modifications, equivalent substitutions and improvements made within the spirit and principles of the present invention should be included within the protection scope of the present invention.

The invention claimed is:

1. A 3D heating component for e-cigarette atomizer, including:
   a plate body having upper and lower surfaces, and
   a plurality of 3D heating units provided on the plate body for guiding, heating and atomizing e-liquid, each of the 3D heating units includes a through hole disposed on the plate body and guide channels distributed regularly at the periphery of the through hole,
   said through hole runs through the upper and lower surfaces of the plate body, and the guide channels are recessed from the surface of the plate body and communicate with the through hole, the guide channels of the adjacent 3D heating units are connected with each other on the surface of the plate body, said plurality of 3D heating units form a regular convex-concave pattern on the surface of the plate body.

2. The 3D heating component of claim 1, further comprising:
   main liquid passages recessed from the upper surface or the lower surface of the plate body, said main liquid passages communicate with the guide channels.

3. The 3D heating component of claim 2, wherein:
   said plate body is a metal plate body, and said plate body has a flat plate shape,
   said guide channels are grooves or potholes recessed from the upper surface or the lower surface of the plate body,
   said grooves include grooves distributed horizontally and grooves distributed vertically, and
   said through holes are located at intersections of the grooves distributed horizontally and the grooves distributed vertically.

4. A 3D grid-like heating sheet for e-cigarette atomizer, comprising:
   a heating sheet body, said sheet body is provided with a plurality of 3D heating unit groups connected in parallel, and each 3D heating unit group is formed by connecting a plurality of 3D heating units and has a center line,
   wherein each 3D heating unit group is regularly distributed with a plurality of first through holes along the center line, a plurality of second through holes are regularly disposed between the center lines of adjacent 3D heating unit groups,
   wherein cross-sectional areas of connecting portions between the first through holes and the adjacent second through holes on the two sides of the center line are equal, said connecting portions are recessed from the surface of the sheet body to form the guide channels, said guide channels communicate with the first through holes and the adjacent second through holes, and the plurality of 3D heating unit groups form a grid-like regular pattern on the surface of the sheet body.

5. The heating sheet of claim 4, wherein:
each heating unit group has a first end, a second end, a third end, and a fourth end, the first end and the second end are oppositely disposed, the third end and the fourth end are oppositely disposed, the first end is used to connect one electrode of a power source, the second end is used to connect another electrode of the power source, and first grooves running through the center line of the heating unit correspond to the first through holes, said third end is provided with third grooves at a position toward the center line of the heating unit group, and the fourth end is provided with fourth grooves at a position toward the center line of the heating unit group, the third and fourth grooves correspond to the second through holes;
wherein, first connecting sections are formed between the first grooves and the third grooves, second connecting sections are formed between the first grooves and the fourth grooves, and the cross-sectional area of the first connecting sections is equal to the cross-sectional area of the second connecting sections.

6. The heating sheet of claim 5, wherein:
two adjacent third grooves in each heating unit group are connected by a third connecting section, two adjacent fourth grooves in each heating unit group are connected by a fourth connecting section, and the third grooves and the fourth grooves adjacent in each heating unit group are connected by a fifth connecting section;
wherein said heating unit groups are horizontally disposed, and the upper surface of the heating units has a flat plate shape, third protruding portions protrude from a lower surface of the third connecting sections, fourth protruding portions protrude from a lower surface of the fourth connecting sections, and fifth protruding portions protrude from a lower surface of the fifth connecting sections, and
wherein a lower surface of the first connecting section, a side surface of the third protruding portion and a side surface of the fifth protruding portion form a first hollow slot, a lower surface of the second connecting section, a side surface of the fourth protruding portion and a side surface of the fifth protruding portion form a second hollow slot, and the first and second hollow slots correspond to the guide channels.

7. A 3D liquid conducting component for e-cigarette atomizing core, comprising:
a body, and
a plurality of 3D liquid conducting units provided on the body for conducting e-liquid, each of the 3D liquid conducting units includes a convex portion and a concave portion adjacently disposed, and the plurality of 3D liquid conducting units are connected and distributed on the body to form a convex-concave staggered regular pattern,
wherein, the plurality of 3D liquid conducting units adjacently disposed form a first liquid conducting zone and a second liquid conducting zone disposed in parallel on the body, said first liquid conducting zone includes a first convex region and a first concave region adjacently disposed, the second liquid conducting zone includes a second convex region and a second concave region adjacently disposed, the first convex region and the second concave region are connected by a first connecting portion, the first concave region and the second convex region are connected by a second connecting portion, a first tearing opening runs through the first connecting portion, and a second tearing opening runs through the second connecting portion.

8. The 3D liquid conducting component of claim 7, wherein:
said body is horizontally disposed, the first convex region is convex upward, the first concave region is concave downward, the first connecting portion connects the lower part of the first convex region and the upper part of the second concave region, and the first tearing opening runs through the first connecting portion in a horizontal direction, the second convex region is convex upward, the second concave region is concave downward, the second connecting portion connects the upper part of the first concave region and the lower part of the second convex region, and the second tearing opening runs through the second connecting portion in the horizontal direction;
the first convex region and the first concave region are connected by a first adapting portion, the second convex region and the second concave region are connected by a second adapting portion, and the first adapting portion and the second adapting portion are both vertically disposed, or the first adapting portion and the second adapting portion are both obliquely disposed, the first tearing opening is disposed in an extending direction of the first liquid conducting zone, and the second tearing opening is disposed in an extending direction of the second liquid conducting zone.

9. A ceramic atomizing core based on a porous heating grid, comprising:
a porous ceramic liquid conducting component, having a vent groove, the porous ceramic liquid conducting component having a hollow cylinder shape;
a 3D grid-like heating sheet, including a plate body provided with a plurality of 3D heating unit groups connected in parallel, and each 3D heating unit group is formed by linearly connecting a plurality of 3D heating units and has a center line; wherein each 3D heating unit is regularly distributed with a plurality of first through holes along the center line, and a plurality of second through holes are regularly disposed between the center lines of the adjacent 3D heating unit groups, wherein the cross-sectional area of a connecting portion between the first through hole and the adjacent second through holes on the two sides of the center line is equal, said connecting portions are recessed from the surface of the sheet body to form guide channels, the guide channels communicate with the first through holes and the adjacent second through holes, and said plurality of 3D heating unit groups form a grid-like regular convex-concave pattern on the surface of the sheet body, and
wherein the 3D heating sheet is disposed on an inner wall of the vent groove of the porous ceramic liquid conducting component.

10. The ceramic atomizing core of claim 9, wherein:
the inner wall of the vent groove is provided with a receiving groove, and the heating member is sintered to the receiving groove by high temperature.

11. The ceramic atomizing core of claim 9, wherein:
the 3D heating sheet is made of a metal material, the periphery of the 3D heating sheet is sleeved with an induction coil, and the heating sheet is located in a varying magnetic field generated by the induction coil.

12. An atomizing core for e-cigarette, including:
a 3D heating component, including a plate body having upper and lower surfaces and provided with a plurality of 3D heating units for guiding, heating and atomizing e-liquid, each of the 3D heating units includes a through hole disposed on the plate body and guide channels distributed regularly at the periphery of the through hole, said through hole runs through the upper and lower surfaces of the plate body, and the guide channels are recessed from the surface of the plate body and communicate with the through hole, the guide channels of the adjacent 3D heating units are connected with each other on the surface of the plate body, said plurality of 3D heating units form a regular convex-concave pattern on the surface of the plate body; and
a 3D liquid conducting component for e-cigarette atomizing core, comprising a body provided with a plurality of 3D liquid conducting units for conducting e-liquid, each of the 3D liquid conducting units includes a convex portion and a concave portion adjacently disposed, and the plurality of 3D liquid conducting units are connected and distributed on the body to form a convex-concave staggered regular pattern, wherein the plurality of 3D liquid conducting units adjacently disposed form a first liquid conducting zone and a second liquid conducting zone disposed in parallel on the body, said first liquid conducting zone includes a first convex region and a first concave region adjacently disposed, the second liquid conducting zone includes a second convex region and a second concave region adjacently disposed, the first convex region and the second concave region are connected by a first connecting portion, the first concave region and the second convex region are connected by a second connecting portion, a first tearing opening runs through the first connecting portion, and a second tearing opening runs through the second connecting portion.

13. An e-cigarette, including
a ceramic atomizing core based on a porous heating grid, said ceramic atomizing core comprises a porous ceramic liquid conducting component having a vent groove and having a hollow cylinder shape, and a 3D grid-like heating sheet disposed on an inner wall of the vent groove of the porous ceramic liquid conducting component, said 3D heating sheet includes a plate body provided with a plurality of 3D heating unit groups connected in parallel, and each 3D heating unit group is formed by linearly connecting a plurality of 3D heating units and has a center line; wherein each 3D heating unit is regularly distributed with a plurality of first through holes along the center line, and a plurality of second through holes are regularly disposed between the center lines of the adjacent 3D heating unit groups, wherein the cross-sectional area of a connecting portion between the first through hole and the adjacent second through holes on the two sides of the center line is equal, said connecting portions are recessed from the surface of the sheet body to form guide channels, the guide channels communicate with the first through holes and the adjacent second through holes, and said plurality of 3D heating unit groups form a grid-like regular convex-concave pattern on the surface of the sheet body, or
a 3D structure atomizing core for e-cigarette, including a 3D heating component, said 3D heating component includes a plate body having upper and lower surfaces and provided with a plurality of 3D heating units for guiding, heating and atomizing e-liquid, each of the 3D heating units includes a through hole disposed on the plate body and guide channels distributed regularly at the periphery of the through hole, said through hole runs through the upper and lower surfaces of the plate body, and the guide channels are recessed from the surface of the plate body and communicate with the through hole, the guide channels of the adjacent 3D heating units are connected with each other on the surface of the plate body, said plurality of 3D heating units form a regular convex-concave pattern on the surface of the plate body; and a 3D liquid conducting component comprising a body provided with a plurality of 3D liquid conducting units for conducting e-liquid, each of the 3D liquid conducting units includes a convex portion and a concave portion adjacently disposed, and the plurality of 3D liquid conducting units are connected and distributed on the body to form a convex-concave staggered regular pattern, wherein the plurality of 3D liquid conducting units adjacently disposed form a first liquid conducting zone and a second liquid conducting zone disposed in parallel on the body, said first liquid conducting zone includes a first convex region and a first concave region adjacently disposed, the second liquid conducting zone includes a second convex region and a second concave region adjacently disposed, the first convex region and the second concave region are connected by a first connecting portion, the first concave region and the second convex region are connected by a second connecting portion, a first tearing opening runs through the first connecting portion, and a second tearing opening runs through the second connecting portion.

* * * * *